United States Patent

Hinkle et al.

(10) Patent No.: US 7,094,848 B2
(45) Date of Patent: Aug. 22, 2006

(54) OLEFIN POLYMERIZATION CATALYST SYSTEM

(75) Inventors: Paul Veinbergs Hinkle, Houston, TX (US); Francis Charles Rix, League City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 247 days.

(21) Appl. No.: 10/436,741

(22) Filed: May 13, 2003

(65) Prior Publication Data

US 2004/0230015 A1 Nov. 18, 2004

(51) Int. Cl.
*C08F 4/44* (2006.01)
*B01J 31/38* (2006.01)

(52) U.S. Cl. .................. 526/161; 526/171; 526/172; 526/348; 502/155; 502/167

(58) Field of Classification Search ................ 526/161, 526/171, 172, 348; 502/155, 167
See application file for complete search history.

(56) References Cited

U.S. PATENT DOCUMENTS

| | | | |
|---|---|---|---|
| 3,180,831 A | * | 4/1965 | Odell et al. |
| 6,037,297 A | | 3/2000 | Stibrany et al. |
| 6,143,857 A | | 11/2000 | Bansleben et al. |
| 6,147,173 A | | 11/2000 | Holtcamp |
| 6,147,174 A | | 11/2000 | Holtcamp et al. |
| 6,180,788 B1 | | 1/2001 | Stibrany |
| 6,197,714 B1 | | 3/2001 | Bansleben et al. |
| 6,197,715 B1 | | 3/2001 | Bansleben et al. |
| 6,211,105 B1 | | 4/2001 | Holtcamp |
| 6,258,903 B1 | | 7/2001 | Mawson et al. |
| 6,265,505 B1 | | 7/2001 | McConville et al. |
| 6,265,513 B1 | | 7/2001 | Murray et al. |
| 6,268,447 B1 | | 7/2001 | Murray et al. |
| 6,281,306 B1 | | 8/2001 | Oskam et al. |
| 6,320,002 B1 | | 11/2001 | Murray et al. |
| 6,333,389 B1 | | 12/2001 | Whiteker et al. |
| 6,340,730 B1 | | 1/2002 | Murray et al. |
| 6,346,584 B1 | | 2/2002 | Wenzel et al. |
| 6,372,868 B1 | | 4/2002 | Szul et al. |
| 6,380,328 B1 | | 4/2002 | McConville et al. |
| 6,399,722 B1 | | 6/2002 | Szul et al. |
| 6,410,664 B1 | | 6/2002 | Bansleben et al. |
| 6,417,303 B1 | | 7/2002 | Stibrany et al. |
| 6,506,704 B1 | | 1/2003 | Bansleben et al. |
| 6,562,922 B1 | | 5/2003 | Bansleben et al. |
| 6,897,275 B1 | | 5/2005 | Wang et al. |
| 2004/0171479 A1 | | 9/2004 | Bazan et al. |

FOREIGN PATENT DOCUMENTS

| | | |
|---|---|---|
| DE | 99556 | 8/1973 |
| EP | 1 217 013 | 5/1996 |
| EP | 0 990 664 | 4/1999 |
| EP | 0 990 664 | 4/2000 |
| EP | 1 217 013 | 6/2002 |
| WO | 96/23010 | 8/1996 |
| WO | 98/30609 | 7/1998 |
| WO | 98/42664 | 10/1998 |
| WO | 98/42665 | 10/1998 |
| WO | 99/30822 | 6/1999 |
| WO | 00/04058 | 1/2000 |
| WO | 00/15676 | 3/2000 |
| WO | 00/29454 | 5/2000 |
| WO | 00/35969 | 6/2000 |
| WO | 00/37509 | 6/2000 |
| WO | 00/37511 | 6/2000 |
| WO | 00/37512 | 6/2000 |

(Continued)

OTHER PUBLICATIONS

Younkin, T.R.; Connor, E.F.; Henderson, J.I.; Friederich, S.K.; Grubbs, R.H.; Bansleben, D.A.; "Neutral, Single-Component Nickel (II) Polyolefin Catalysts That Tolerate Heteroatoms", Science 2000, 287, 460-462.

(Continued)

*Primary Examiner*—Robert D. Harlan
(74) *Attorney, Agent, or Firm*—Catherine L. Bell

(57) ABSTRACT

This invention relates to a compound represented by the formula:

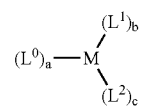

wherein M is selected from groups 3–11 of the periodic table;

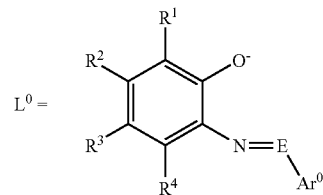

$L^1$ represents a formal anionic ligand, $L^2$ represents a formal neutral ligand, a is an integer greater than or equal to 1; b is greater than or equal to 0; c is greater than or equal to 1, E is nitrogen or phosphorus, $Ar^0$ is arene, $R^1$–$R^4$ are, each independently, selected from hydrogen, hydrocarbyl, substituted hydrocarbyl or functional group, provided however that $R^3$ and $R^4$ do not form a naphthyl ring, N is nitrogen and O is oxygen.

This invention further relates to a process to oligomerize and/or polymerize unsaturated monomers using the above compositions, optionally combined with an activator.

32 Claims, 3 Drawing Sheets

FOREIGN PATENT DOCUMENTS

| | | |
|---|---|---|
| WO | 00/56781 | 9/2000 |
| WO | 00/56785 | 9/2000 |
| WO | 00/56786 | 9/2000 |
| WO | 00/56787 | 9/2000 |
| WO | 01/30860 | 5/2001 |
| WO | 01/30861 | 5/2001 |
| WO | 01/30862 | 5/2001 |
| WO | 01/40325 | 6/2001 |
| WO | 01/40330 | 6/2001 |
| WO | 01/44321 | 6/2001 |
| WO | 02/06358 | 1/2002 |
| WO | 02/10227 | 2/2002 |
| WO | 02/18452 | 3/2002 |
| WO | 02/32968 | 4/2002 |
| WO | 02/38629 | 5/2002 |
| WO | 02/45854 | 6/2002 |
| WO | 02/46243 | 6/2002 |
| WO | 02/46250 | 6/2002 |
| WO | 02/51884 | 7/2002 |

OTHER PUBLICATIONS

Wang, C. Friederich, S.; Younkin, T.R.; Grubbs, R.H.; Bansleben, D.A.; Day, M.W.; "Neutral Nickel (II)-Based Catalysts for Ethylene Polymerization", *Organometallics* 1998, 17, 3149-3151.

Hicks, F.; Brookhart, M.; "A Highly Active Anilinotropone-Based Neutral Nickel (II) Catalyst for Ethylene Polymerization", *Organometallics* 2001, 20, 3217-3219.

Connor, E.F.; Younkin, T.R.; Henderson, J.I.; Hwang, S.; Grubbs, R.H.; Roberts, W.P.; Litzau, J.J., "Linear Functionalized Polyethylene Prepared with Highly Active Neutral Ni (II) Complexes", *J. Pol. Sci. A.* 2002, 40, 2842-2854.

Schroeder, D.L.; Keim, w.; Zuideveld, M.A.; Mecking, S, "Ethylene Polymerization by Novel, Easily Accesible Catalysts Based on Nickel (II) Diazene Complexes", *Macromolecules*, 2002, 35, 6071-6073.

Laali, K.; Szele, I.; Zollinger, H., "Dediazoniation of Arendediazonium Ion. Part XXII, Reactions of 2,6-Dialkyl-Substituted Benzenediazonium Ions in Super Acids, Acetonitrile and Acetone" *Helvetica Chimica Acta* 1983, 66, 1737-1747.

Petrillo, G.; Novi, M.; Garbarino, G.; Filiberti, M., The Reaction Between Arendiazonium Tetrafloroborates and Alkaline Thiocarboxylates in DMSO: A Convenient Access to Aryl Thiolesters and other Aromatic Sulfur Derivatives: *Tetrahedron* 1989, 45, 7411-7420.

Drent et al., "Palladium Catalysed Copolymerisation of Ethene with Alkylacrylates: Polar Comonomer Built into the Linear Polymer Chain", Chem. Commun. 2002, 744-745.

Stribrany et al., "Cu Catalysts for Homo- and Copolymerization of Olefins and Acrylates", Polymeric Materials: Science & Engineering 2002, 86, 325.

Stibrany et al., "Cu Catalysts for Homo- and Copolymerization of Olefins and Acrylates", Beyond Metallocenes: Next-Generation Polymerization Catalysts, ACS Symposium Series 857, Washington, DC. 2003, 222-230.

Wang et al., "Novel Nickel Catalysts for Ethylene/Polar Monomer Copolymerization", Polymeric Materials: Science & Engineering 2002, 86, 322.

Johnson et al., "Copolymerization of Ethylene and Propylene with Functionalized Vinyl Monomers by Palladium(II) Catalysts", J. Am. Chem. Soc. 1996, 118, 267-268.

Mecking et al., "Mechanistic Studies of the Palladium-Catalyzed Copolymerization of Ethylene and $\alpha$-Olefins with Methyl Acrylate", J. Am. Chem. Soc. 1998, 120, 888-899.

Johnson et al., "Copolymerization of Ethylene and Acrylates by Nicket Catalysts", Polymeric Materials: Science & Engineering 2002, 86, 319.

Liu et al., "Ethylene Polymerization and Ethylene/Methyl 10-Undecenoate Copolymerization Using Nickel(II) and Palladium(II) Complexes Derived from a Bulky P,O Chelating Ligand", Organometallics 2002, 21, 2836-2838.

Ittel et al., "Late-Metal Catalysts for Ethylene Homo- and Copolymerization", Chem. Rev. 2000, 100, 1169-1203.

Gibson et al., "Advances in Non-Metallocene Olefin Polymerization Catalysts", Chem. Rev. 2003, 103, 283-315.

Stibrany et al., "Polymerization and Copolymerization of Olefins and Acrylates by Bis(benzimidazole) Copper Catalysts", Macromolecules 2003, 36, 8584-8586.

Grubbs et al., "Neutral Single-Component Nickel (II) Polyolefin Catalysts That Tolerate Heteroatoms", Science, vol. 287, (Jan. 27, 2000), pp. 460-462.

Wang Et al., "Neutral Nickel(II)-Based Catalysts for Ethylene Polymerization", Organometallics, 1998, 17, pp. 3149-3151.

* cited by examiner

OLEFIN POLYMERIZATION CATALYST SYSTEM

FIELD OF THE INVENTION

This invention relates to novel phenoxide-containing transition metal compounds and to processes to polymerize or oligomerize unsaturated monomers using phenoxide-containing transition metal compounds and polymers produced therefrom.

BACKGROUND OF THE INVENTION

The present invention is directed toward new transition metal compounds containing bidentate E-phenoxide ligands and formal neutral ligands that are useful for the oligomerization and polymerization of olefins. Bidentate E-phenoxide ligands form 6-membered metallacycle rings when bound to a transition metal. These compounds, and optionally an activator, can be used to oligomerize or polymerize unsaturated monomers such as olefins.

Other polymerization catalysts employing bidentate ligands based on phenoxide that form six-membered metallacycle rings have been reported in the art. Mitsui has reported low activity transition metal complexes containing azo-phenoxide ligands (European Patent EP-A1 0 990 664). Low activity, low molecular weight catalysts that use an azo-phenoxide ligand based upon a naphthyl ring have also been reported in the literature (*Macromolecules*, 2002, 35, 6071). Catalysts based upon keto-amide structures have been reported by Dupont (WO 98/30609). These show poor activity and low molecular weight or poor molecular weight control. Imine-phenoxide catalysts based on nickel have been reported both by Grubbs (Science 2000, 287, 460; *Organometallics* 1998, 17, 3149; *J. Pol. Sci. A.* 2002, 40, 2842; WO 98/42665; WO 2000/56786; WO 2000/56787; WO 2000/56781) and Dupont researchers (WO 98/30609). These imine-phenoxide systems were examined alongside the azo-phenoxide catalysts reported here and the imine-phenoxide systems were shown to give lower molecular weight polymer.

Other references of interest include:
1. Younkin, T. R.; Connor, E. F.; Henderson, J. I.; Friederich, S. K.; Grubbs, R. H.; Bansleben, D. A. Science 2000, 287, 460
2. Wang, C. Friederich, S.; Younkin, T. R.; Li, R. T.; Grubbs, R. H.; Bansleben, D. A.; Day, M. W. *Organometallics* 1998, 17, 3149.
3. Johnson, L. K.; Bennett, A. M. A.; Wang, L.; Parthasarathy, A.; Hauptman, E.; Simpson, R. D.; Feldman, J.; Coughlin, E. B. WO 98/30609
4. Bansleben, D. A.; Friederich, S. K.; Younkin, T. R.; Grubbs, R. H.; Wang, C.; Li, R. T. WO 98/42664
5. Bansleben, D. A.; Friederich, S. K.; Younkin, T. R.; Grubbs, R. H.; Wang, C.; Li, R. T. WO 98/42665
6. Bansleben, D. A.; Connor, E. F.; Grubbs, R. H.; Henderson, J. I.; Younkin, T. R.; Nadjadi, A. R. WO 2000/56786
7. Bansleben, D. A.; Connor, E. F.; Grubbs, R. H.; Henderson, J. I.; Younkin, T. R.; Nadjadi, A. R. WO 2000/56787
8. Bansleben, D. A.; Friedrich, S. K.; Grubbs, R. H.; Li, R. T.; Connor, E. F.; Roberts, W.P. Wo 2000/56781
9. Hicks, F.; Brookhart, M. *Organometallics* 2001, 20, 3217
10. Connor, E. F.; Younkin, T. R.; Henderson, J. I.; Hwang, S.; Grubbs, R. H.; Roberts, W. P.; Litzau, J. J. *J. Pol. Sci. A.*. 2002, 40, 2842
11. Schroeder, D. L.; Keim, w.; Zuideveld, M. A.; Mecking, S, *Macromolecules*, 2002, 35, 6071
12. Matsui, S.; Nitabaru, M.; Tsuru, K.; Fujita, T.; Suzuki, Y.; Takagi, Y.; Tanaka, H. EP 0 990 664 A1
13. Laali, K.; Szele, I.; Zollinger, H., *Helvetica Chimica Acta* 1983, 66, 1737
14. Petrillo, G.; Novi, M.; Garbarino, G.; Filiberti, M., *Tetrahedron* 1989, 45, 7411

SUMMARY OF THE INVENTION

This invention relates to a compound represented by the formula:

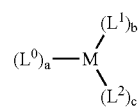

wherein M is selected from groups 3–11 of the periodic table;

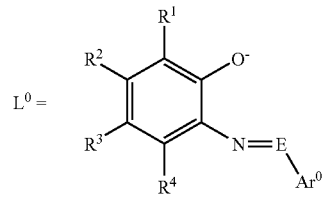

$L^1$ represents a formal anionic ligand, $L^2$ represents a formal neutral ligand, a is an integer greater than or equal to 1; b is an integer greater than or equal to 0; c is an integer greater than or equal to 1, E is nitrogen or phosphorus, $Ar^0$ is arene, $R^1$–$R^4$ are, each independently, selected from hydrogen, hydrocarbyl, substituted hydrocarbyl or functional group, provided however that $R^3$ and $R^4$ do not form a naphthyl ring, N is nitrogen, and O is oxygen.

This invention further relates to a process to oligomerize and/or polymerize unsaturated monomers using the above compositions, optionally combined with an activator.

DETAILED DESCRIPTION OF THE INVENTION

Figure 1:
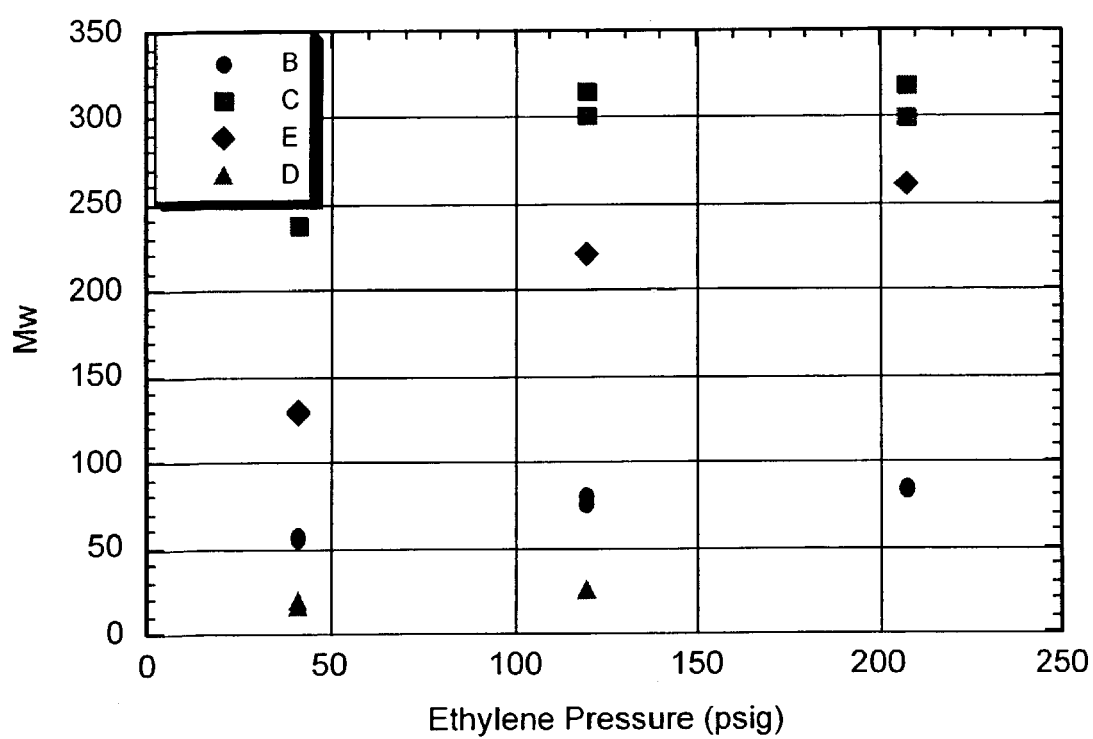
FIG. 1 is a plot of Mw (k, calculated using polystyrene standard) versus ethylene pressure.
Figure 2:
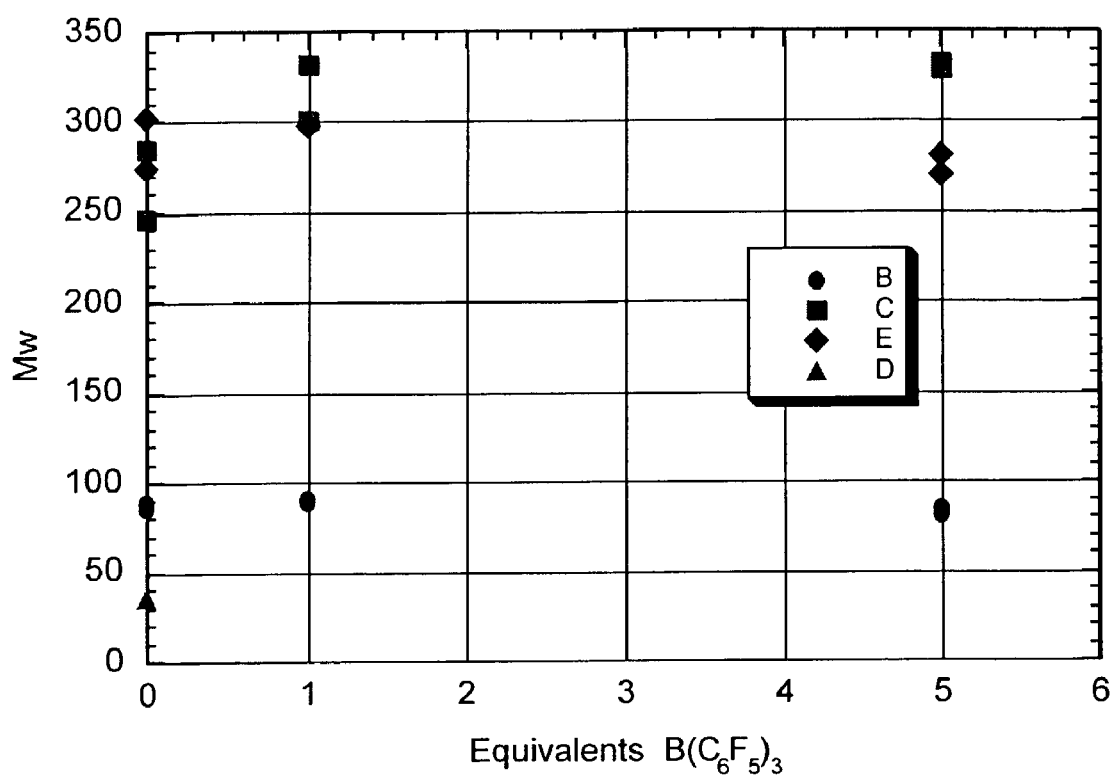
FIG. 2 is a plot of Mw (k, calculated using polystyrene standard) versus equivalent of $B(C_6F_5)_3$ at 264 psig. The plot indicates that at 264 psig the Mw capabilities of the azo precatalysts are comparable or better than the corresponding imine catalysts.
Figure 3:
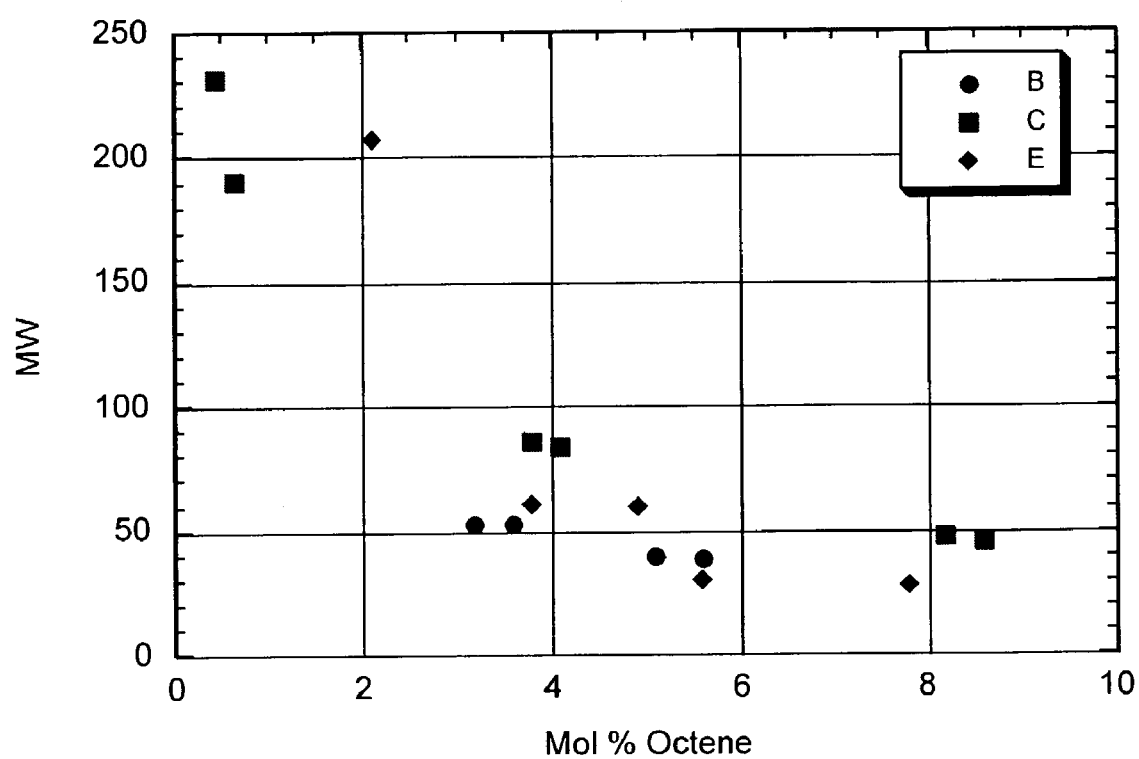
FIG. 3 is a comparison of Mw (k) vs. mol % octene incorporated from the data in Table 3.

This invention relates to a new class of catalyst compounds that may be combined with one or more activators to oligomerize or polymerize any unsaturated monomer.

For the purposes of this invention and the claims thereto when a polymer is referred to as comprising a monomer, the momomer present in the polymer is the polymerized form of the monomer. For the purposes of this invention and the claims thereto when a polymer is referred to as comprising an olefin, the olefin present in the polymer is the polymerized form of the olefin. In the description herein the transition metal catalyst compound may be described as a catalyst precursor, a pre-catalyst compound, a transition metal complex or a catalyst compound, and these terms are used interchangeably. A catalyst system is a combination of a transition metal catalyst compound and an activator. An activator is also interchangeably referred to as a cocatalyst. In addition, a reactor is any container(s) in which a chemical reaction occurs.

As used herein, the numbering scheme for the Periodic Table Groups is used as in CHEMICAL AND ENGINEERING NEWS, 63(5), 27 (1985).

Further for purposes of this invention Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, and TMS is trimethylsilyl.

This invention further relates to processes for preparing oligomers and/or polymers of unsaturated monomers, such as polar monomers and or olefins comprising contacting a transition metal compound (as described herein) and, optionally, an activator with the monomers.

The metal compound preferably contains at least one E-phenoxide ligand ($L^0$), and at least one formal neutral ligand ($L^2$). The remaining ligands in the coordination sphere of the metal compound typically are such that the compound attains a d electron count of 14–18. The d electron count is the formal sum of the metal's d electrons plus those contributed by the ligands.

Preferred E-phenoxide metal compounds are represented by formula:

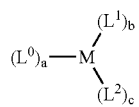

1 wherein:

M is selected from groups 3–11 of the periodic table, preferably group 4 or 10, more preferably Ti or Ni;

$L^0$ represents an E-phenoxide ligand represented by the formula:

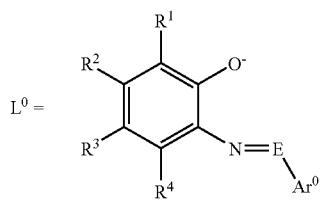

wherein:

E is nitrogen or phosphorus, preferably nitrogen;

$Ar^0$ is arene;

$R^1$–$R^4$ are each independently selected from hydrogen, hydrocarbyl, substituted hydrocarbyl or functional group, provided that $R^3$ and $R^4$ do not form a naphthyl ring;

$L^1$ represents a formal anionic ligand;

$L^2$ represents a formal neutral ligand;

a is an integer greater than or equal to 1, preferably a=1, 2, 3 or 4, preferably a=1 or 2;

b is an integer greater than or equal to 0, preferably b is 0, 1, 2, 3, 4, 5 or 6, more preferably b=0, 1 or 2; and c is an integer greater than or equal to 1, preferably c=1, 2, 3 or 4, more preferably 1 or 2.

The metal compound may be neutral or a charged species with a counterion.

The metal compound preferably contains at least one formal neutral ligand coordinated to the metal in addition to the nitrogen or phosphorus of the E-phenoxide ligand(s). Formal neutral ligands are defined as ligands that are neutral, with respect to charge, when formally removed from the metal in their closed shell electronic state. Formal neutral ligands contain at least one lone pair of electrons, pi-bond or sigma bond that are capable of binding to the transition metal. Formal neutral ligands may also be polydentate when more than one formal neutral ligand is connected via a bond or a hydrocarbyl, substituted hydrocarbyl or a functional group tether. A formal neutral ligand may be a substituent of another metal compound, either the same or different, such that multiple compounds are bound together.

Formal neutral ligands may be composed of combinations of hydrocarbyl, substituted hydrocarbyl, and functional groups. Non-limiting examples of formal neutral ligands are ethers, ketones, esters, alcohols, carboxylic acids, amines, imines, azo, nitriles, heterocycles, phosphines, thioethers, alkyls, alkenes, alkynes, and arenes.

For purposes of this invention and the claims thereto "ZETA FORMAL NEUTRAL LIGANDS" are defined to be formal neutral ligands represented by the following formulae:

$P(C(CH_3)_3)_3$ $P(C_6H_{11})_3$ $P(CH(CH_3)_2)_3$
$P(CH_2CH_2CH_3)_3$ $P(CH_2CH_3)_3$ $P(CH_3)_3$
$P(C_6H_4OCH_3)_3$ $P(CH_2C_6H_5)_3$ $P(C_6H_4CH_3)$
$P(C_6H_5)_3$ $P(CH=CH_2)_3$ $P(C_6H_4F)_3$ $P(C_6H_4Cl)_3$
$P(C_2H_5)_2C_6H_5P(CH_3)_2C_6H_5$ $P(C_6H_5)_2CH_3$
$P(C_6H_5)_2NMe_2$ $P(C_6H_5)CH_2C_6H_5$ $P(C_6H_5)_2$
$(C_6H_4OCH_3)$ $P(C_6H_5)(CH_2C_6H_5)_2$ $P(C_6H_5)_2$
$(CH=CH_2)$ $P(C_6H_5)_2(C_6H_4F)$ $P(OCH_2CH_3)$
$(C_6H_5)_2$ $P(OCH(CH_3)_2)_2C_6H_5$ $PH(C_6H_5)_2$
$P(OCH_2CH_2CH_3)_2C_6H_5$ $P(OC_6H_5)(C_6H_5)_2$
$P(C_6H_5)_2C_6F_5$ $PPh_2(C_6H_4Cl)$ $P(C_6H_3(OCH_3)_2)_3$
$P(C_6H_5)_2(C_6H_4N(CH_3)_2)$ $P(C_6H_2(CH_3)_3)_3$
$P(C_6H_5)_2(C_6H_2(CH_3)_3)$ $P(C_6H_5)(C_6F_5)_2$
$P(C_6F_5)_3$ $P(C_{10}H_7)_3$ $Me_3P=CH_2$ $(C_6H_5)_3$
$P=CH$, $H_2C=CH_2$ $H_2C=CHCH_3$
$H_2C=CH_2CH_2CH_3$ $CH_3CH=CHCH_3$
$H_2C=CH_2CH_2CH_2CH_3$ $CH_3CH=CHCH_2CH_3$
$H_2C=CH_2CH_2CH_2CH_2CH_3$
$CH_3CH=CHCH_2CH_2CH_3$
$CH_3CH_2CH=CHCH_2CH_3$
$CH_3CH=CHCH_2CH_2CH_2CH_3$
$CH_3CH_2CH=CHCH_2CH_2CH_3$
$H_2C=CH_2CH_2CH_2CH_2CH_2CH_2CH_3$
$CH_3CH_2CH_2CH=CHCH_2CH_2CH_3$ $CH_3CH$
$(CH_3)CH=CH_2$ $C(CH_3)_3CH=CH_2$ $(CH_3)_2$
$C=CH$, $CH_3CH_2CH(CH_3)CH=CH_2$
$H_2C=CH.CH=CH_2$ $CH_3CH=CH.CH=CH_2$
$CH_3CH=CH.CH=CHCH_3$ $H_2C=C(CH_3)$—
$(CH_3)C=CH_2$ $(CH_3CH_2)_2C=CH_2$ $H_2C=C$
$(CH_3)$—$CH=CH_2$ $H_2C=CH$—$CH_2)_1$—
$CH=CH_2$ $H_2C=CH$—$CH_2)_2$—$CH=CH_2$
$H_2C=CH$—$CH_2)_3$—$CH=CH_2$ $H_2C=CH$—
$CH_2)_4$—$CH=CH_2$ $H_2C=CH$—$CH_2)_1$—$CH=C$
$(CH_3)_2$ $H_2C=CH$—$CH_2)_2$—$CH=C(CH_3)_2$
$H_2C=CH$—$CH_2)_3$—$CH=C(CH_3)_2$
$H_2C=CH$—$CH_2)_4$—$CH=C(CH_3)_2$ $(C_6H_5)$
$CH=CH$—$CH=CH_2$ $(C_6H_5)CH=CH$—
$CH=CH(C_6H_5)$ $CH_2=CH$—$CH_2CH=CHCH_3$
$CH_2=CH$—$CH_2C(CH_3)=CHCH_3$ $CH_2=C$
$(CH_3)$—$CH_2CH=CHCH_3$ $CH_2=C(CH_3)$—
$CH_2CH_3$

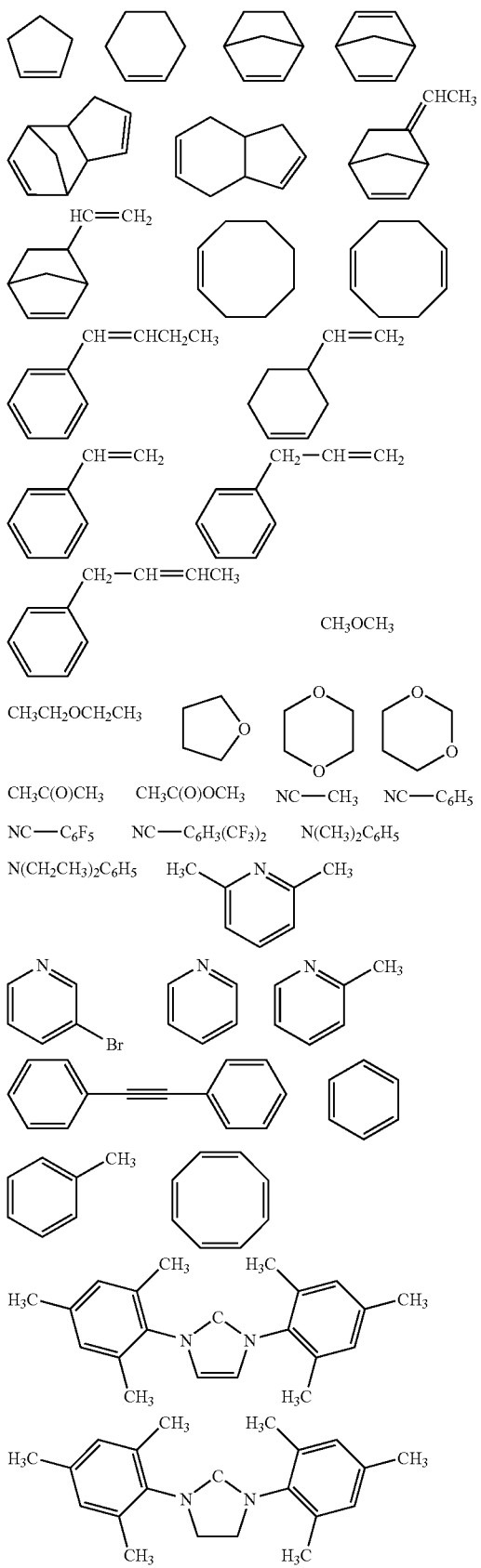

Formal anionic ligands are defined as ligands that are anionic, with respect to charge, when formally removed from the metal in their closed shell electronic state. Formal anionic ligands include hydride, halide, hydrocarbyl, substituted hydrocarbyl or functional group. Non-limiting examples of formal anionic ligands include hydride, fluoride, chloride, bromide, iodide, alkyl, aryl, alkenyl, alkynyl, allyl, benzyl, acyl, trimethylsilyl. Formal anionic ligands may also be polydentate when more than one formal anionic ligand is connected via a bond or a hydrocarbyl, substituted hydrocarbyl or a functional group tether. A formal anionic ligand may be a substituent of another metal compound, either the same or different, such that multiple compounds are bound together.

For purposes of this invention and the claims thereto "ZETA-FORMAL ANIONIC LIGANDS" is defined to be the group of formal anionic ligands represented by the following formulae:

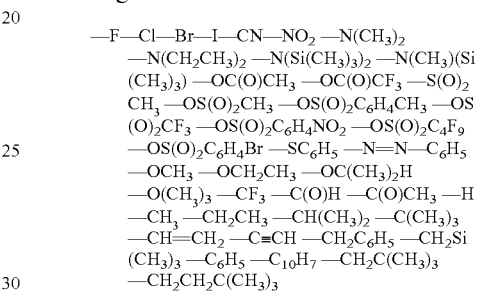

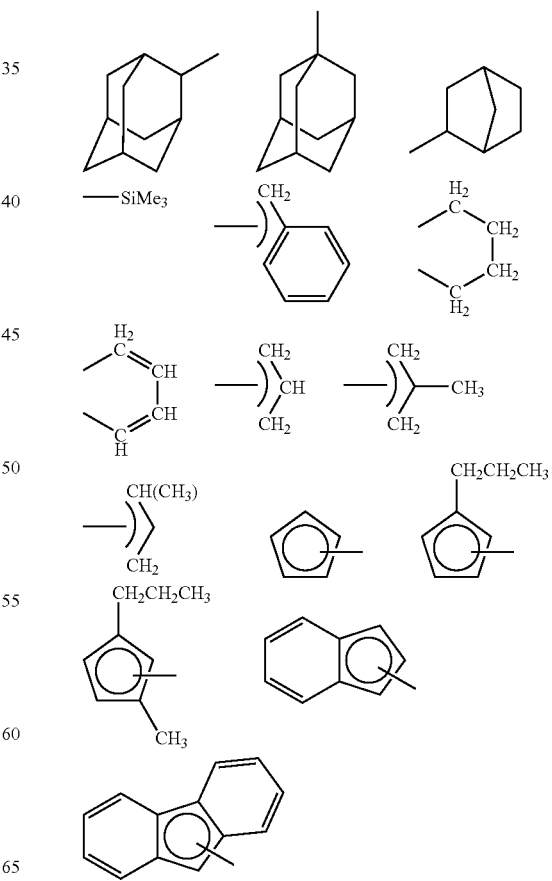

More preferred formal anionic ligands include: —F, —Cl, —Br, —I, —N(CH$_3$)$_2$, —OCH$_3$, —H, —CH$_3$, —C$_6$H$_5$, -Allyl, -Benzyl, —CH$_2$Si(CH$_3$)$_3$.

Preferred non-limiting examples of formal anionic ligand that comprises a functional group include:

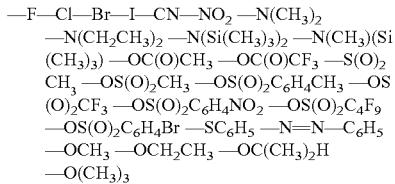

More preferred formal anionic ligands that comprise functional groups include: —F, —Cl, —Br, —I, —N(CH$_3$)$_2$, —OCH$_3$.

Using this nomenclature of anionic and neutral ligands, the ligands may be categorized as combinations of anionic and neutral ligands as when L$^1$ and L$^2$ are connected via a bond or a hydrocarbyl, substituted hydrocarbyl or a functional group tether. Preferred non-limiting examples of L$^1$, L$^2$ that meet this definition include ethyl, norbornyl, allyl, benzyl, CH$_2$CH$_2$C(O)Me, 1-(2-N(CH$_3$)$_2$C$_6$H$_4$), acetylacetonate. The capability of hydrocarbyl groups, such as ethyl and norbornyl, to coordinate as a formal ligand (M-C sigma bond) and a formal neutral ligand, via an agostic 3 center-2 interaction between C, H and M is well recognized.

Monodentate ligands that are capable of multiple bonding to the metal may be categorized as combinations of anionic and neutral ligands. Ligands which display this behavior are functional groups that in addition to being a formal anionic ligand, have at least one pair of electrons, either localized or in a bonding arrangement with another atom or atoms, that also interact with the metal.

Non-limiting examples of such ligands are oxo, imido, carbene and Preferred non-limiting examples include:

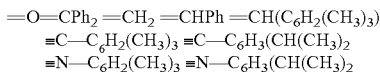

Preferred non-limiting examples of hydrocarbyl groups include:

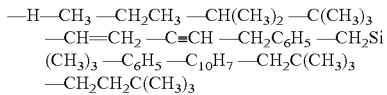

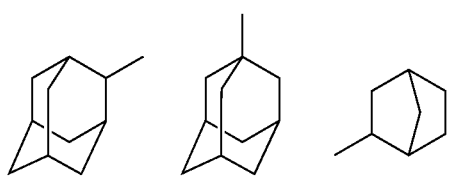

—SiMe$_3$

Substituted hydrocarbyl radicals (also called substituted hydrocarbyls) are radicals in which at least one hydrocarbyl hydrogen atom has been substituted with at least one heteroatom or heteroatom containing group.

Preferred non-limiting examples of substituted hydrocarbyls include:

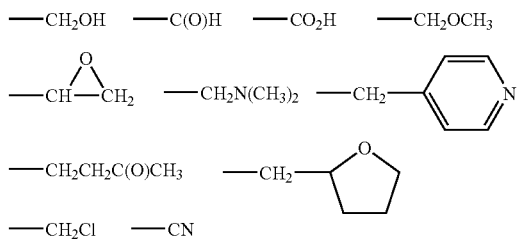

The term "hydrocarbyl radical" is sometimes used interchangeably with "hydrocarbyl" throughout this document. For purposes of this disclosure, "hydrocarbyl radical" encompasses radicals containing carbon hydrogen and optionally silicon atoms, preferably 1 to 100 carbon atoms, hydrogen and optionally silicon. These radicals can be linear, branched, or cyclic including polycyclic. These radicals can be saturated, partially unsaturated or fully unsaturated, and when cyclic, may be aromatic or non-aromatic.

In some embodiments, the hydrocarbyl radical is selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. For this disclosure, when a radical is listed it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

An arene is a substituted or unsubstituted aromatic hydrocarbon. Arenes may be monocyclic, polycyclic, hydrocarbon ring assemblies or fused ring systems. Arenes may be substituted or unsubstituted heterocyclics, polyheterocyclics, heterocyclic ring assemblies or fused heterocyclic ring systems. (In the formulae below, Z$^+$ is a cation, preferably a metal or metal compound of groups 1, 2, 11, or 12 and A$^-$ is an anion.) For purposes of this invention and the claims thereto the term "ZETA-ARENES" is defined to be the group of arenes represented by the following formulae:
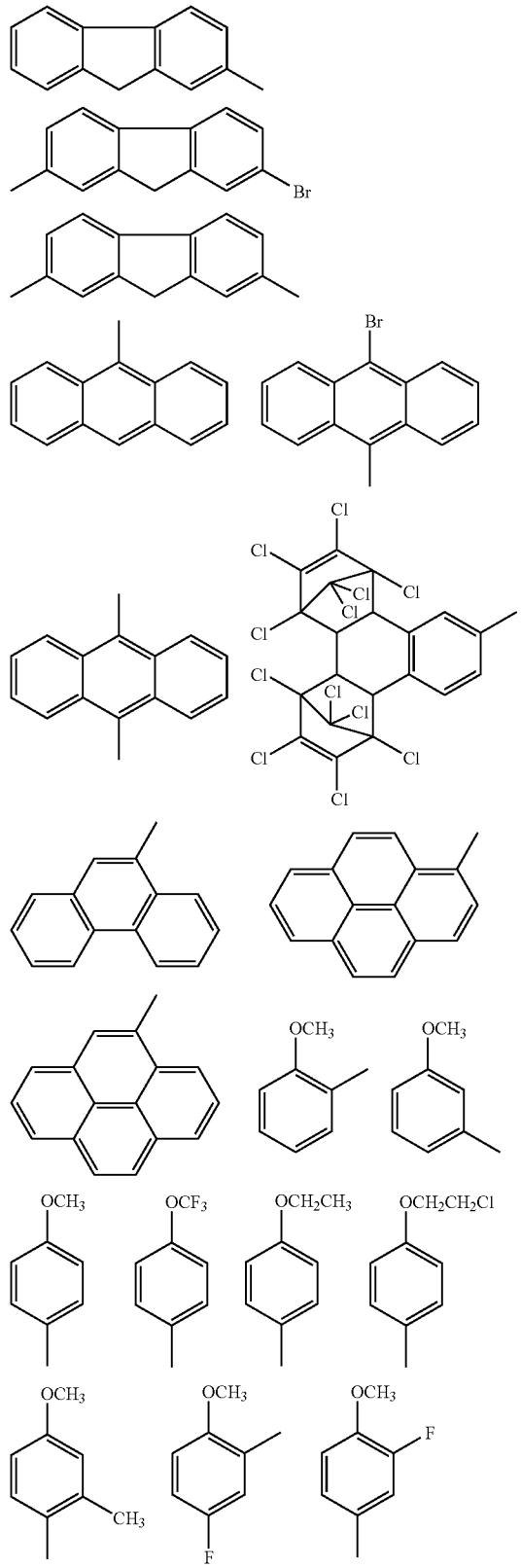
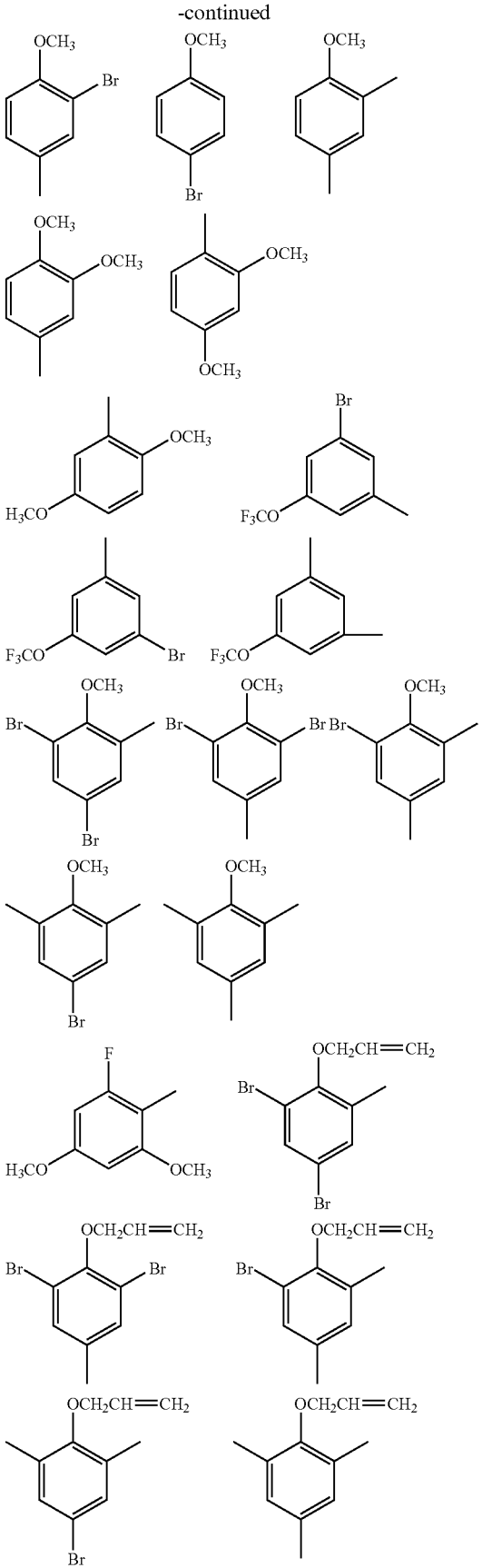

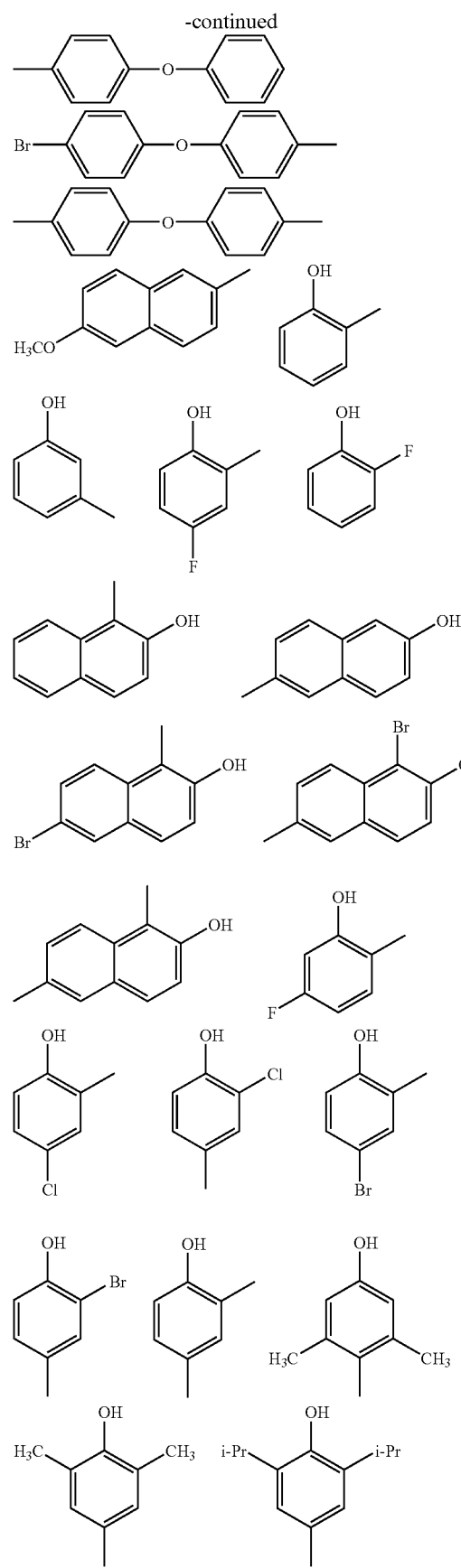

-continued
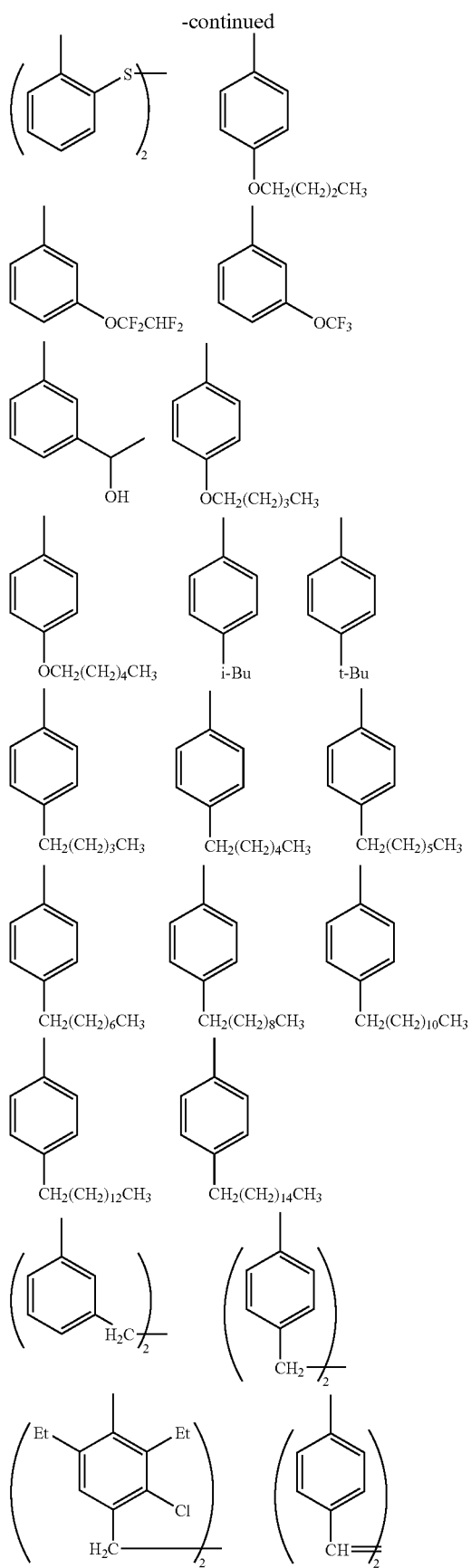
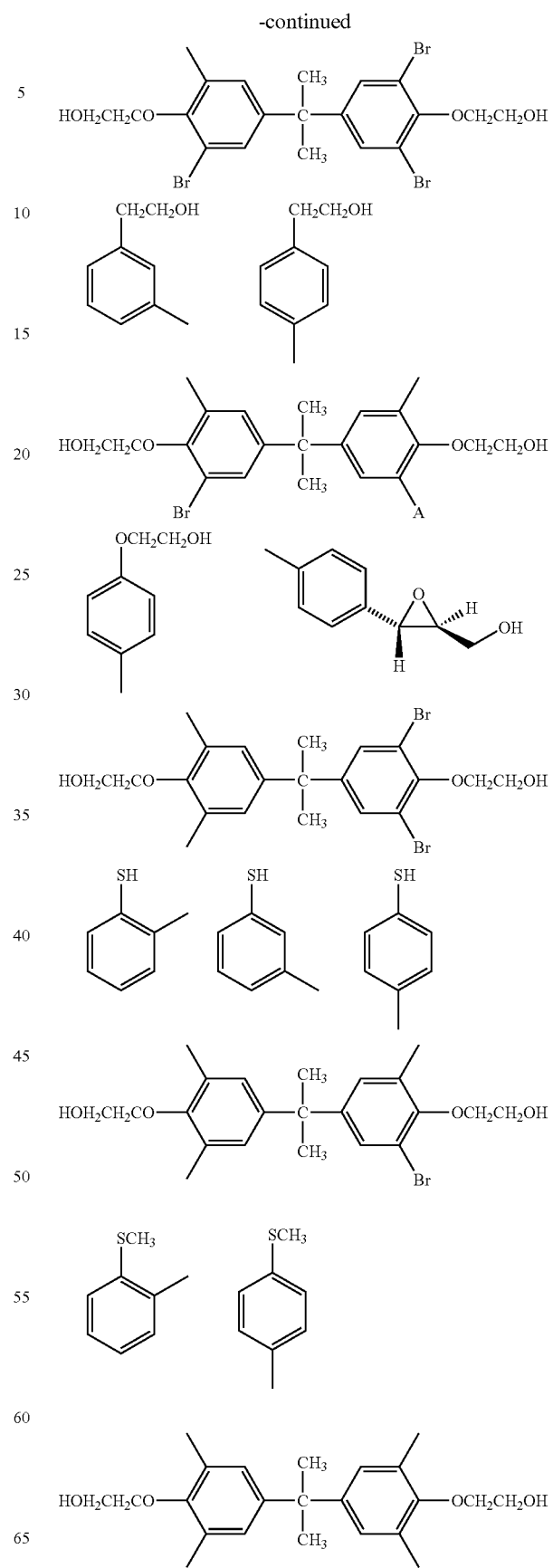

-continued
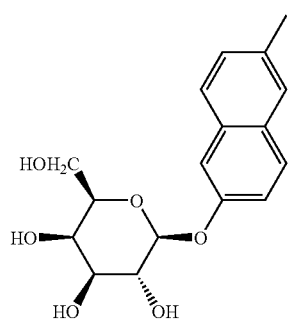
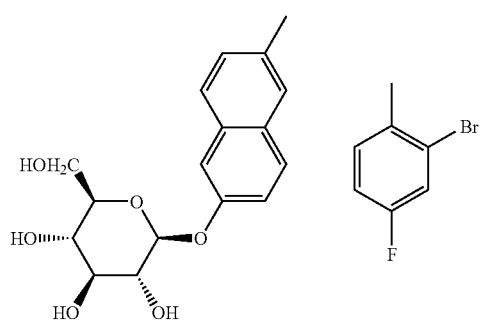
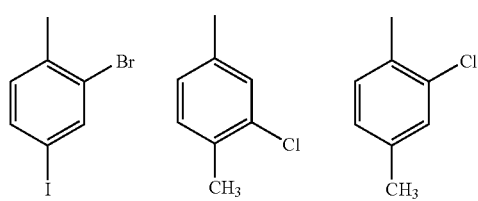
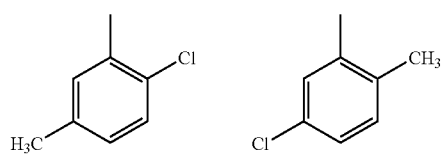
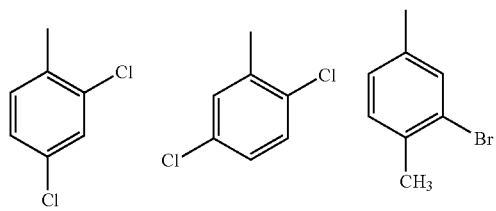
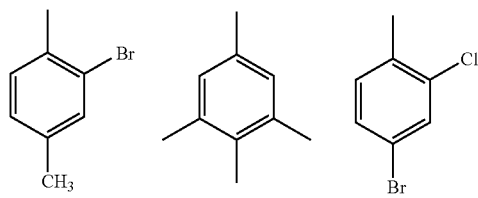
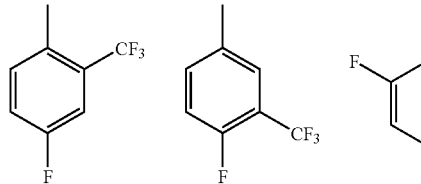
-continued
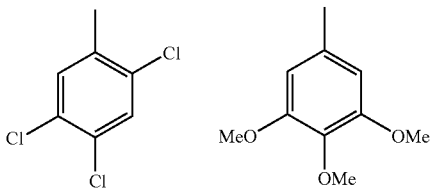
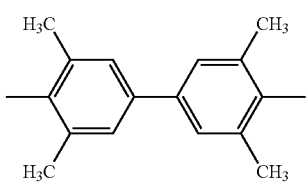
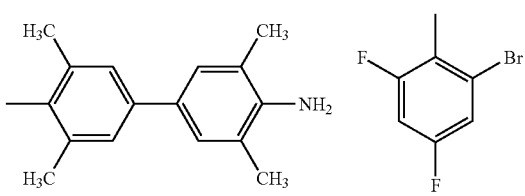
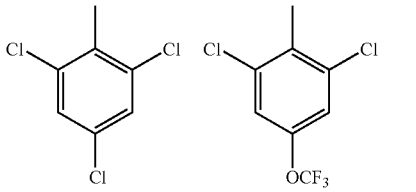
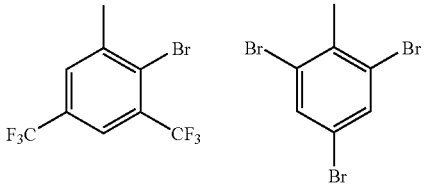
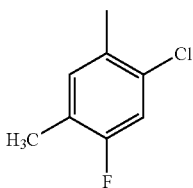
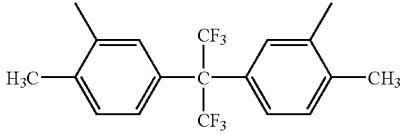
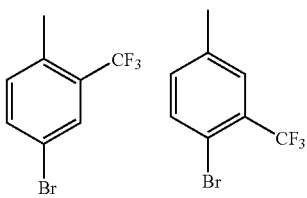
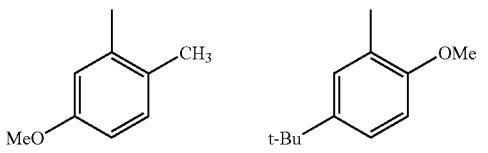

-continued
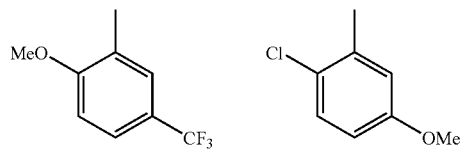
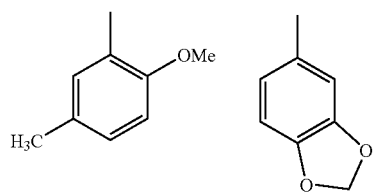
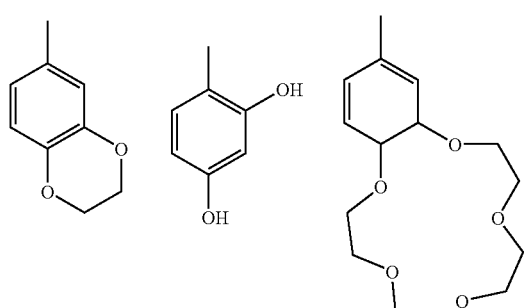
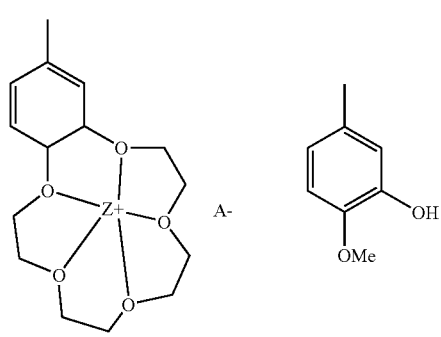
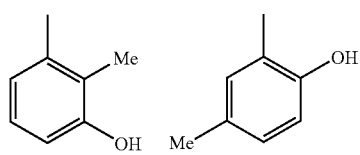
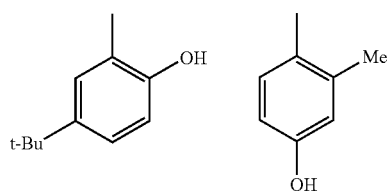
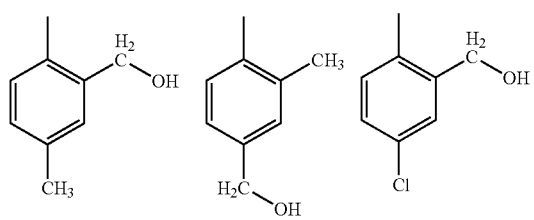
-continued
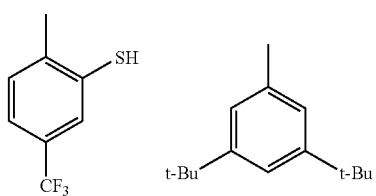
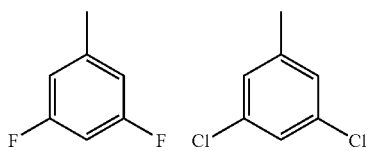
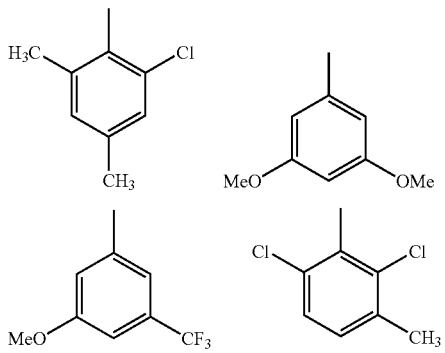
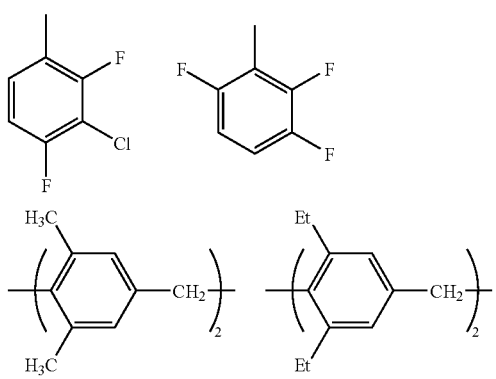
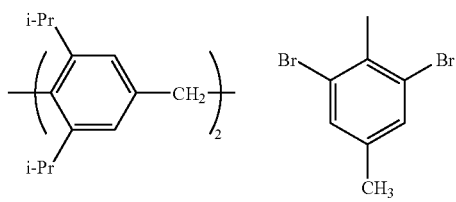
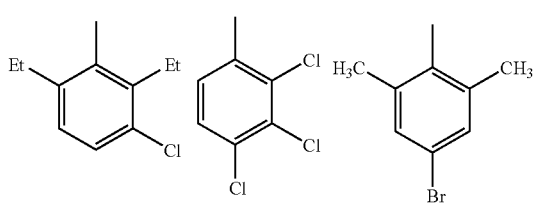
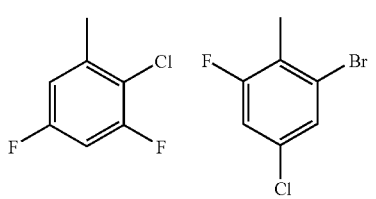

-continued
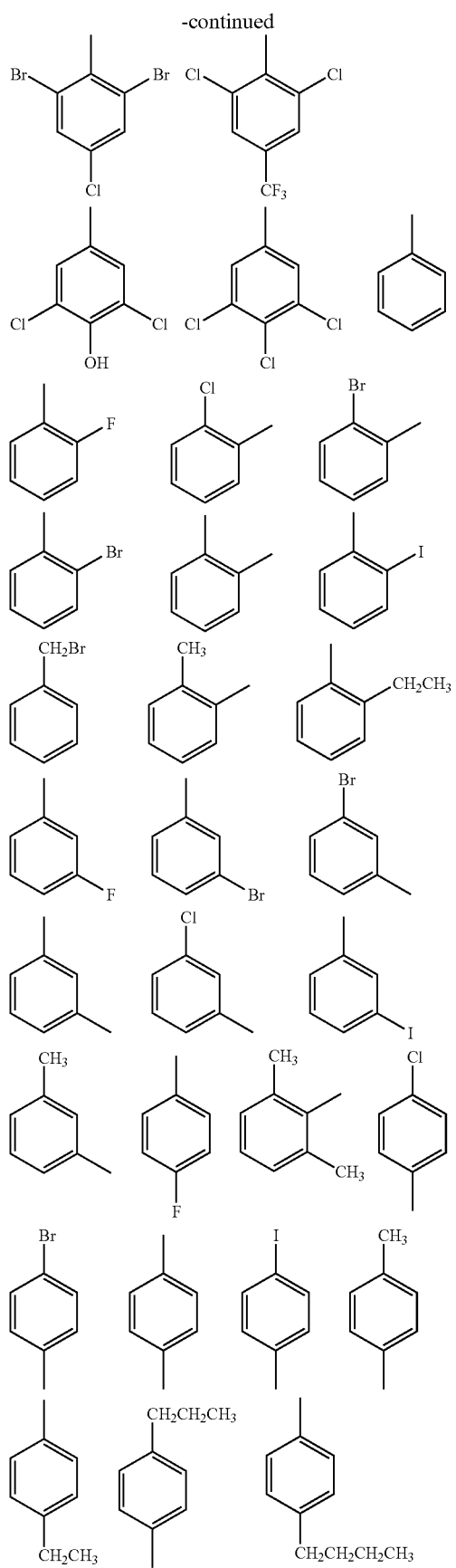
-continued
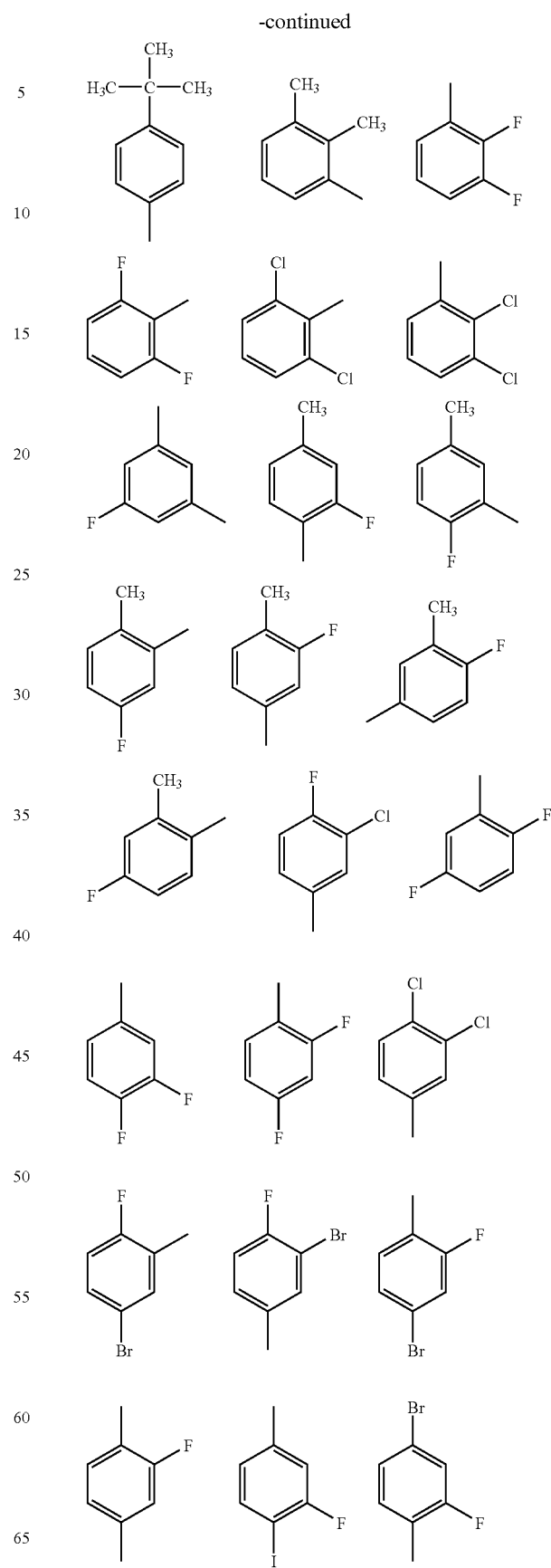

-continued
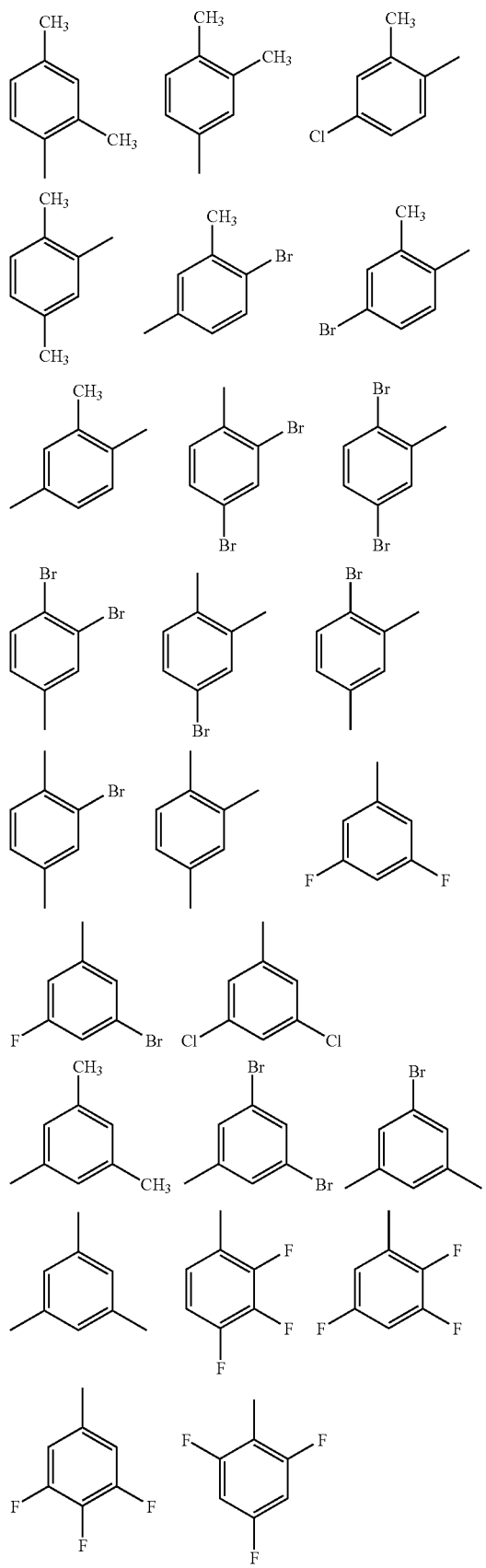
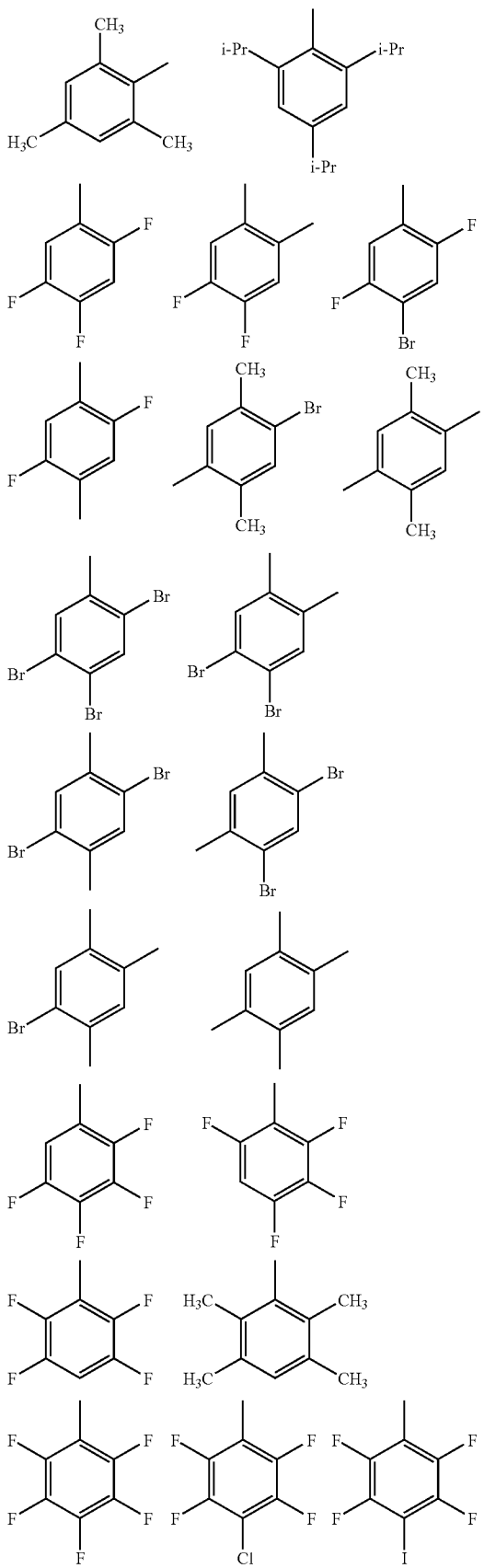

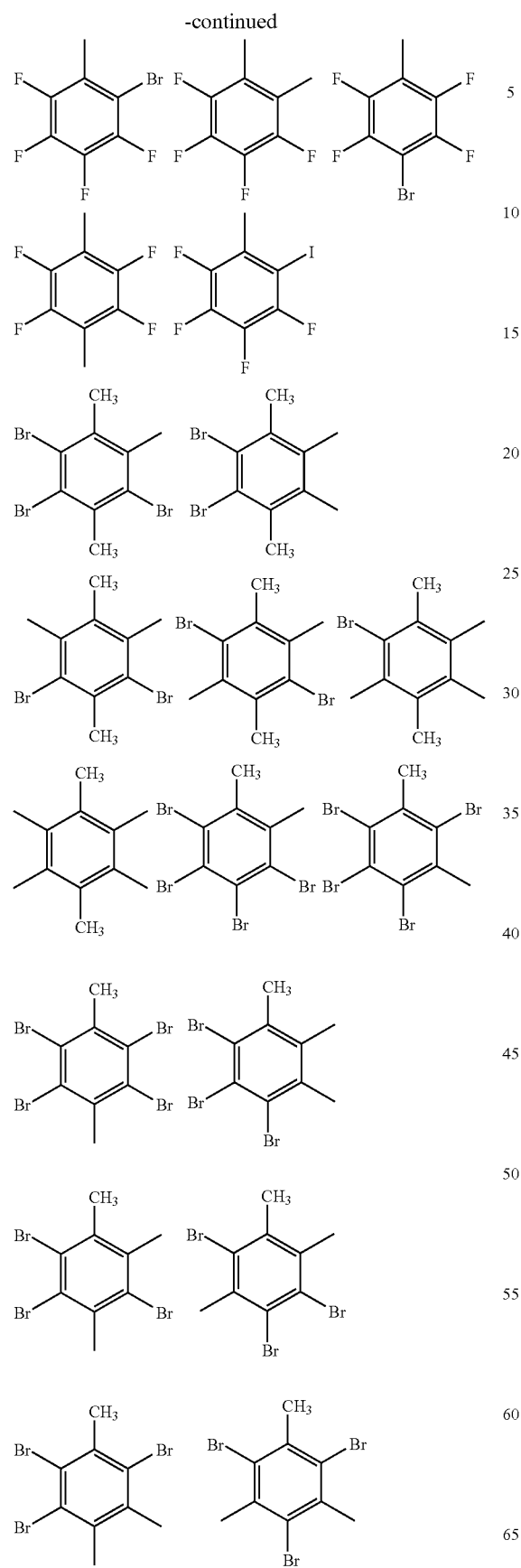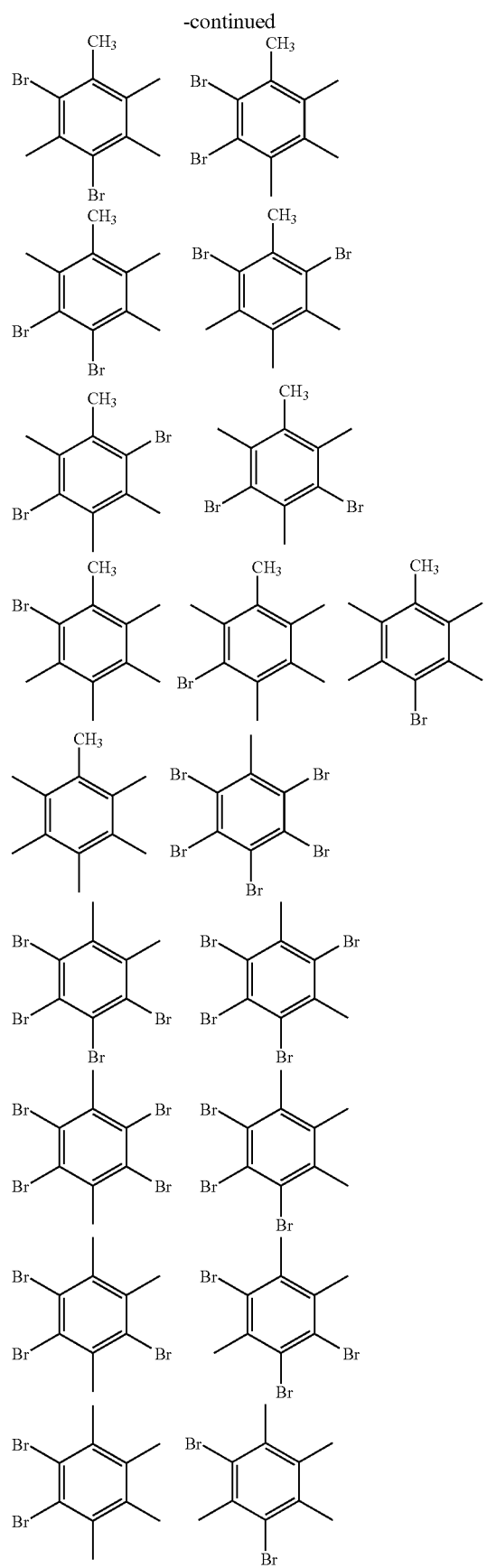

-continued
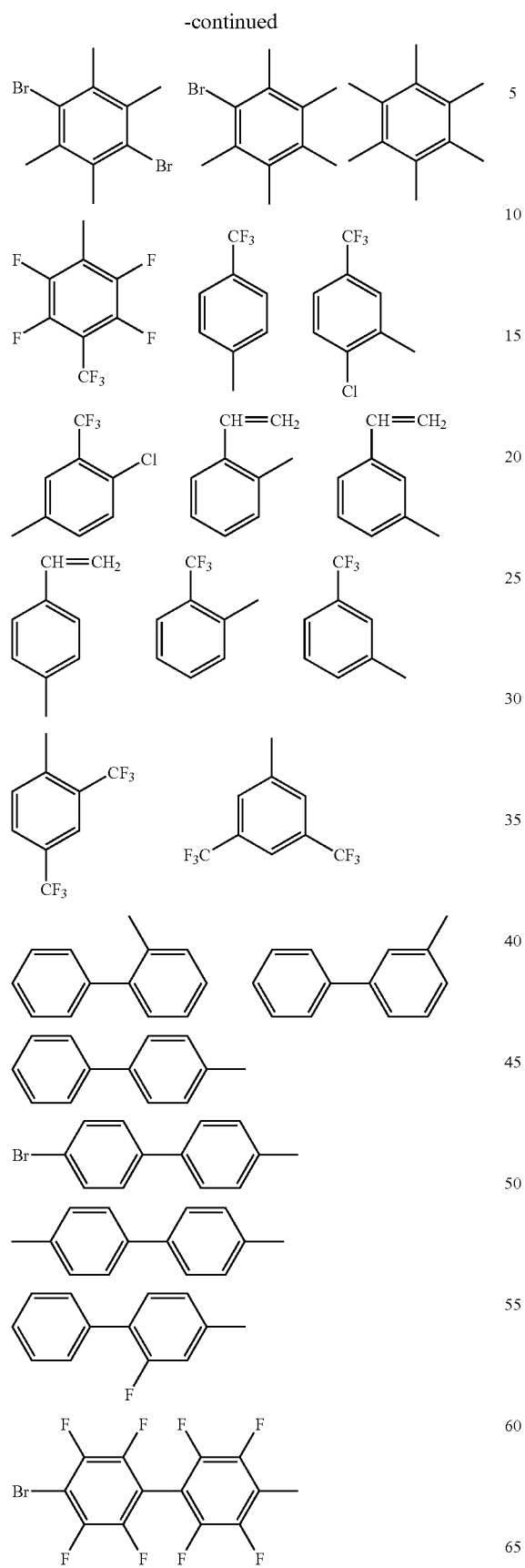
-continued
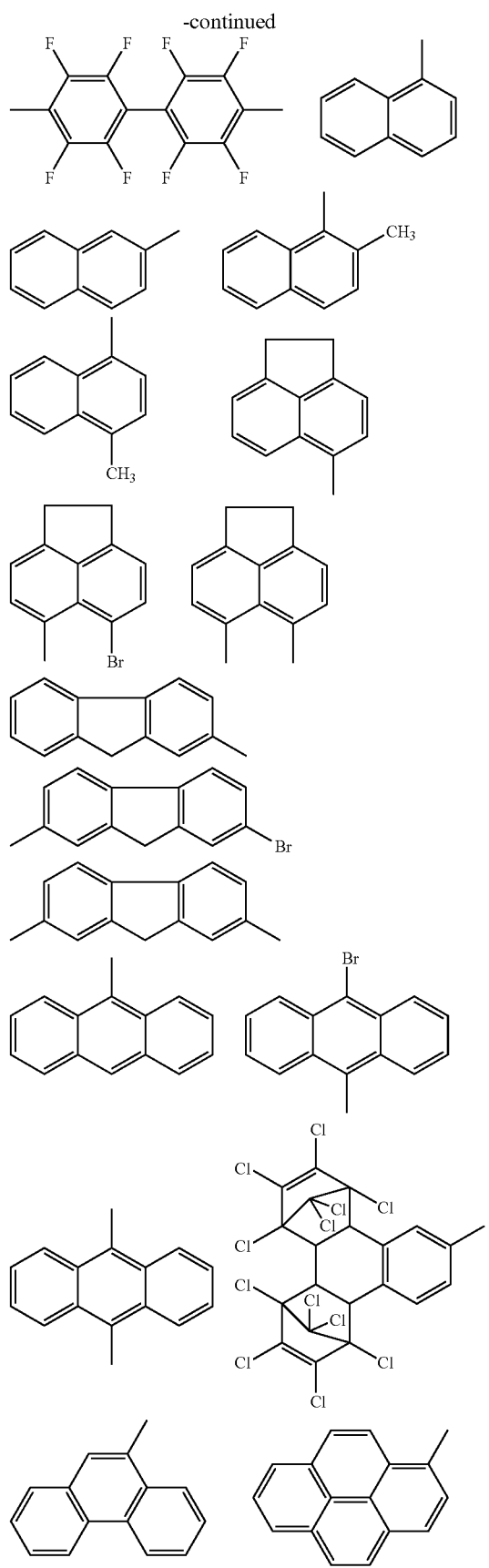

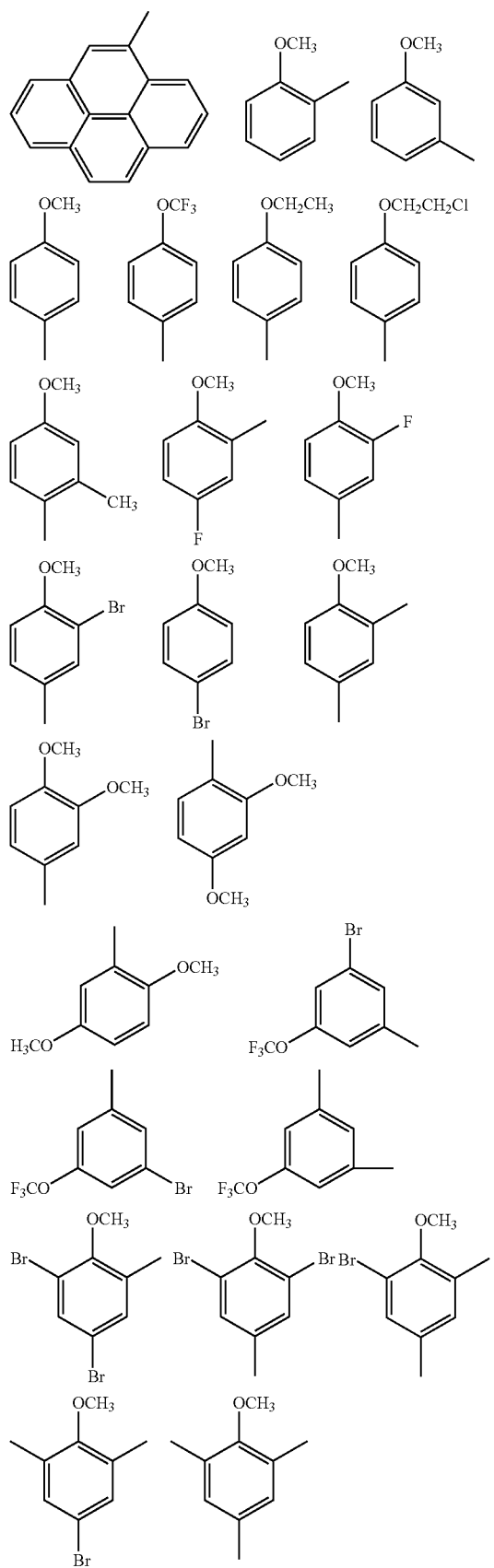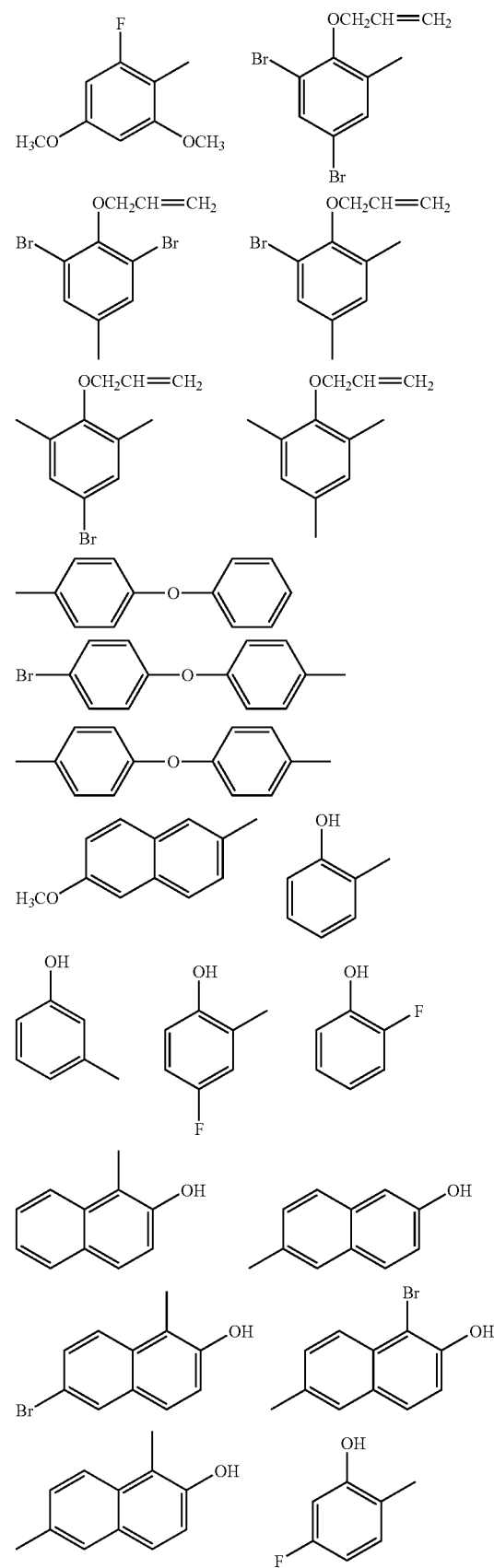

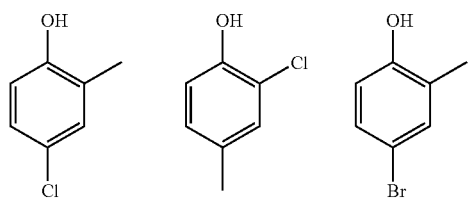
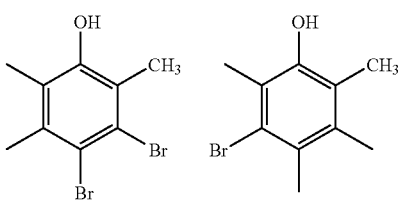
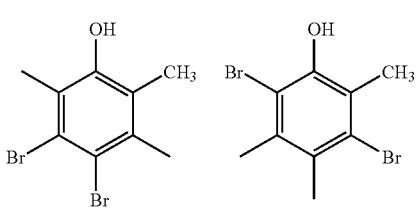
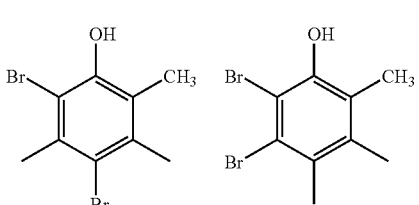
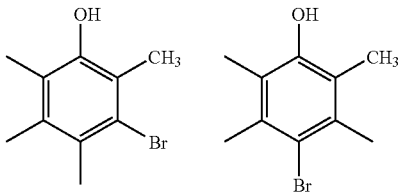
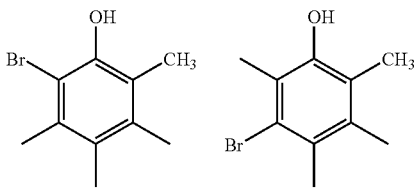
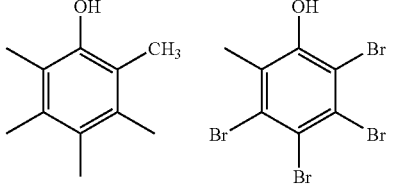
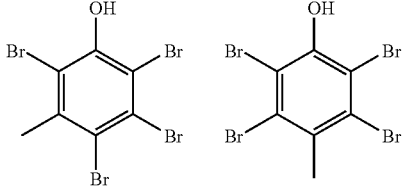

-continued
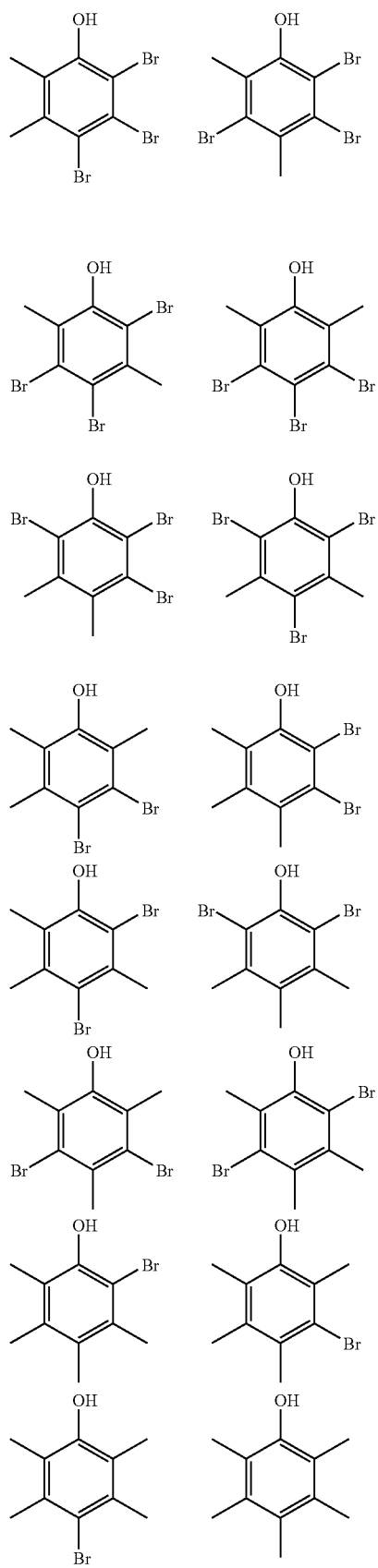
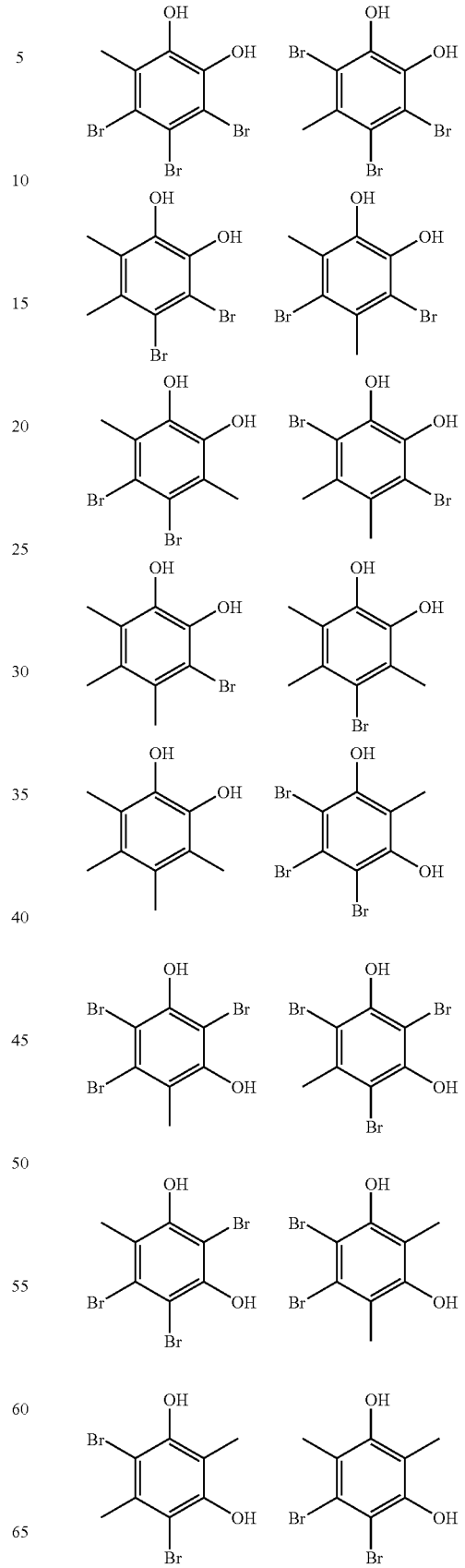

-continued
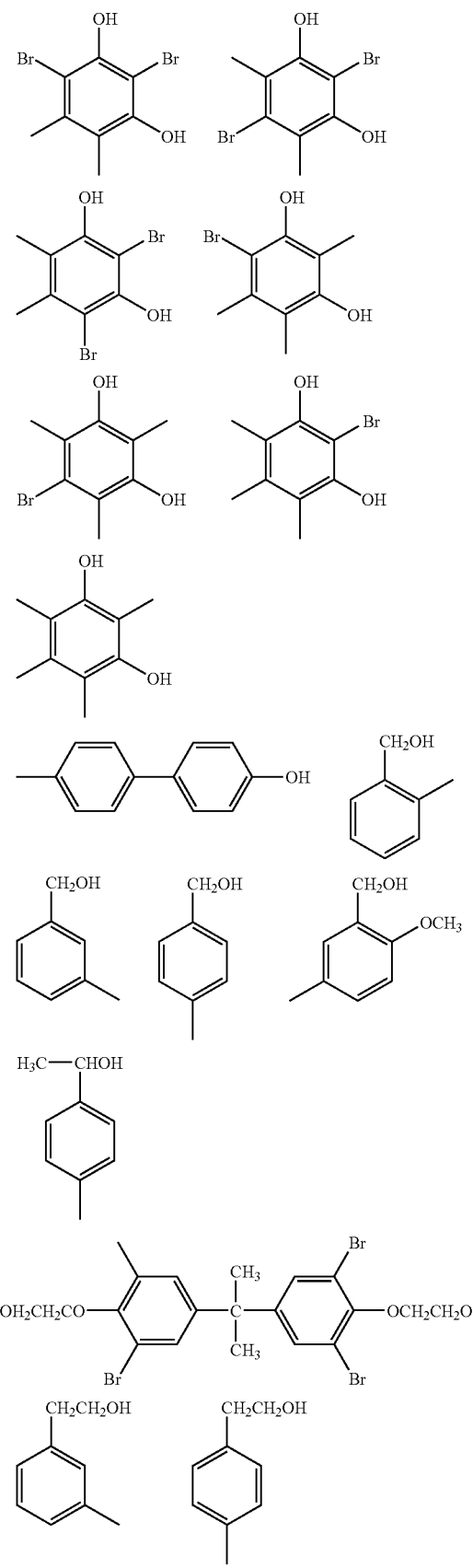
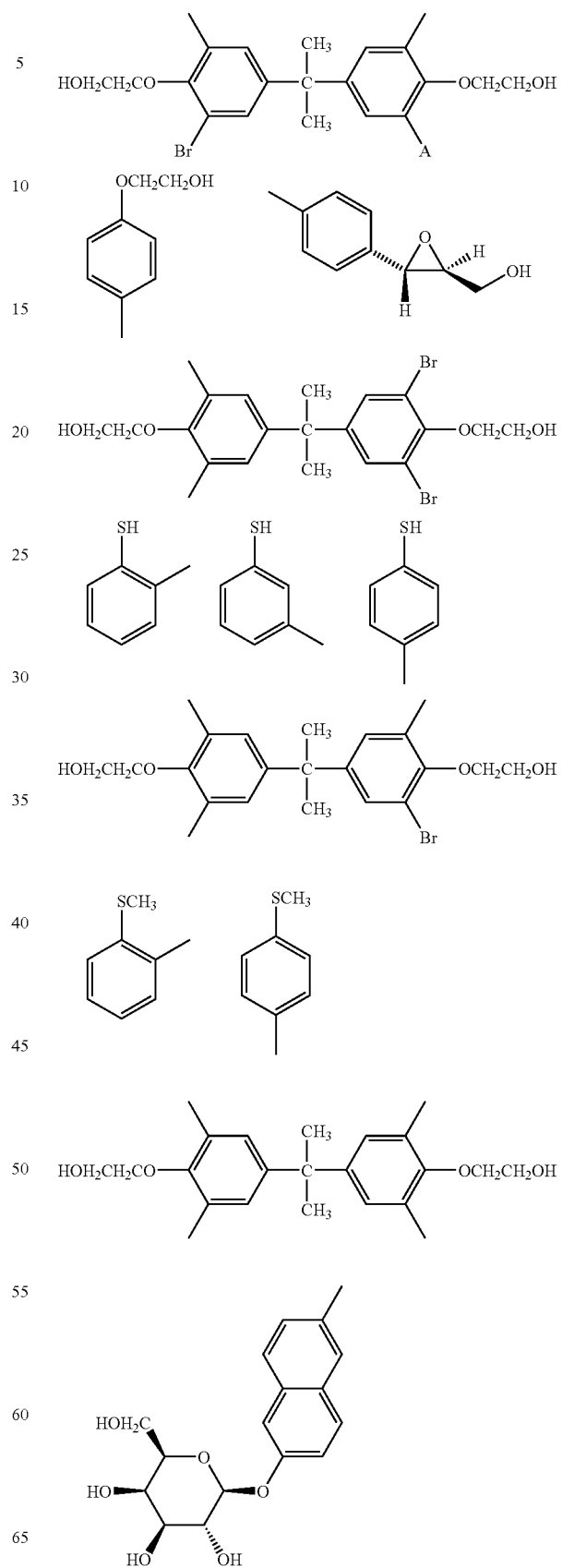

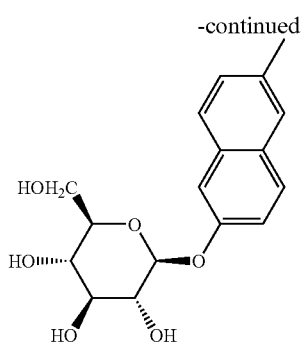

Functional groups are heteroatoms of groups 1–17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica.

The nomenclature of d electron count, anionic ligands, neutral ligands, and oxidation state used here are described in length in the texts: Hegedus, L. S. Transition Metals in the Synthesis of Complex Organic Molecules 2nd Ed, University Science Press, 1999, Sausalito, Calif. and Collman, J. P. et. al. Principles and Applications of Organotransition Metal Chemistry. University Science Press, 1987, Sausalito, Calif.

Preferred E-phenoxide metal compounds include those represented by the following formulae:

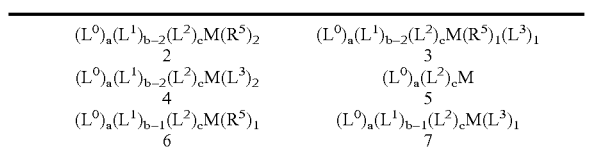

wherein:

M is selected from groups 3–11 of the periodic table, preferably group 4 or 10, more preferably Ti or Ni.

$L^0$ represents an E-phenoxide ligand represented by the formula:

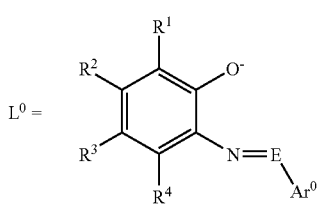

$L^1$ represents a formal anionic ligand;
$L^2$ represents a formal neutral ligand;
$L^3$ represents a formal anionic ligand that comprises a functional group;
a is greater than or equal to 1, preferably a=1, 2, 3 or 4, preferably a=1 or 2;
b is greater than or equal to 0, preferably b is 0, 1, 2, 3, 4, 5 or 6, more preferably b=0, 1 or 2, provided that b is not 0 or 1 in formula 2, 3 or 4 and b is not 0 in formula 6 or 7;
c is greater than or equal to 1, preferably c=1, 2, 3 or 4, more preferably 1 or 2;
E is nitrogen or phosphorus, preferably nitrogen;
N is nitrogen;
O is oxygen;
$Ar^0$ is an arene;
$R^1$–$R^4$ are each independently hydrogen, a hydrocarbyl, a substituted hydrocarbyl or a functional group, provided that $R^3$ and $R^4$ do not form a naphthyl ring; and
$R^5$ is a hydride, a hydrocarbyl or a substituted hydrocarbyl.

Additional preferred E-phenoxide metal compounds include those represented by the following formulae:

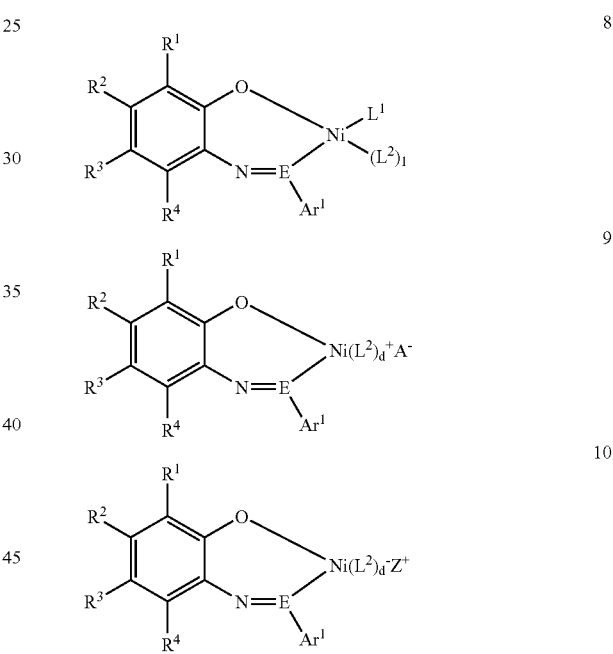

E is nitrogen or phosphorus, preferably nitrogen;
N is nitrogen;
O is oxygen
$Ar^1$ is arene; preferably one or more of:

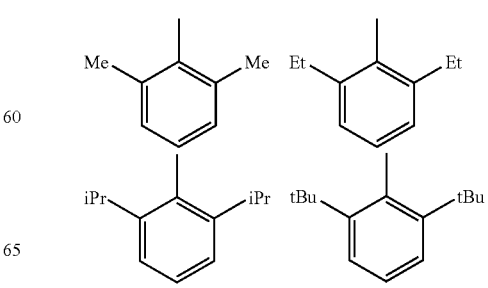

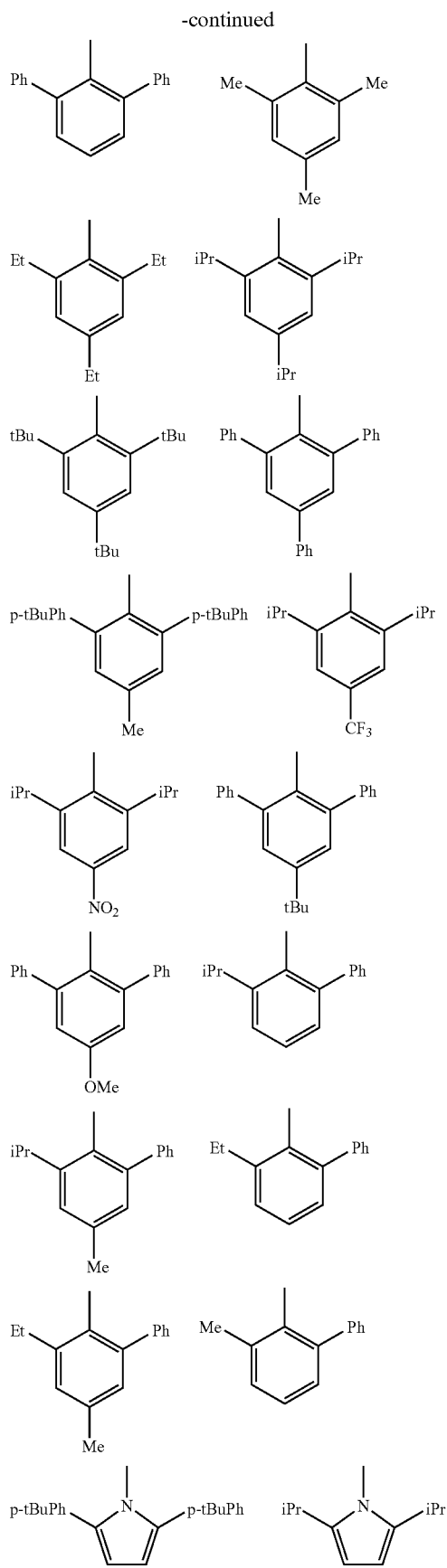

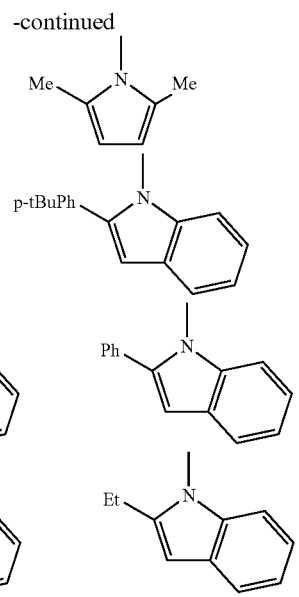

R¹–R⁴ are each independently hydrogen, a hydrocarbyl, a substituted a hydrocarbyl or a functional group, provided that $R^3$ and $R^4$ do not form a naphthyl ring;

$L^1$ represents a formal anionic ligand;

$L^2$ represents a formal neutral ligand;

"d" equals 1, 2 or 3, preferably 2;

$A^-$ is an anion that may or may not coordinate to Ni or may coordinate weakly to N; $A^-$ may be a non-coordinating anion, a substituted hydrocarbon or a functional group, preferably $A^-$ comprises one or more halides, carboxylates, phosphates, sulfates, sulfonates, borates, aluminates, alkoxides, thioalkoxides, anonic substituted hydrocarbons, or anionic metal complexes;

$Z^+$ is a cation, preferably a metal or metal complex of groups 1, 2, 11, or 12.

Preferably, the metal compound contains at least one formal neutral ligand coordinated to the metal in addition to the nitrogen or phosphorus of the E-phenoxide ligand(s).

The nickel compounds contain one E-phenoxide ligand and at least one formal neutral ligand. The remaining ligands in the coordination sphere of the metal compound are such that the compound attains a d electron count of 14–18. The nickel compound may be neutral or a charged species with an appropriate counterion.

Preferred metal compounds include those containing one azo-phenoxide ligand, one formal neutral ligand, and one formal anionic ligand.

Additional preferred azo-phenoxide metal compounds are represented by formula 11 and its steroisomers:

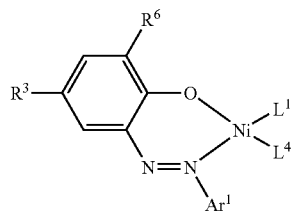

11

$L^1$ represents a formal anionic ligand;
$R^3$ is hydrogen, a hydrocarbyl, a substituted hydrocarbyl or a functional group;
$R^6$ is $C(R^7)_e$, e=2 or 3, $R^7$ is a hydrocarbon, a substituted hydrocarbon, or a functional group, two $R^7$ groups may be part of a common arene ring when e=2; Preferred non-limiting examples of $R^6$ include t-butyl, adamantyl, phenyl, naphthyl, anthracenyl.
$Ar^1$ is an arene;
$L^4$, is a formal neutral ligand, coordinated to the nickel in addition to the nitrogen of the azo-phenoxide ligand, based on carbon, nitrogen or phosphorus, preferably one or more alkenes, alkynes, nitriles, pyridines, aryl phosphines and phosphorus ylides. Non-limiting preferred examples of $L^4$ include:

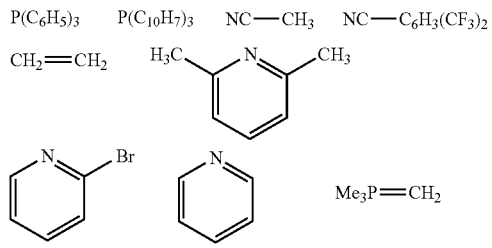

Particularly preferred azo-phenoxide compounds are represented by formula 12:

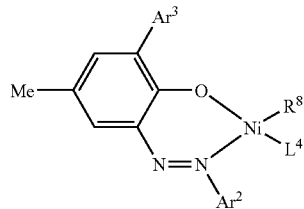

12 wherein:
$L^4$ represents a formal neutral ligand based on carbon, nitrogen or phosphorus preferably one or more alkenes, alkynes, nitriles, pyridines, aryl phosphines and or phosphorus ylides;

$R^8$ represents a formal anionic ligand which may be hydrogen or a hydrocarbon, preferably a hydride, methyl, ethyl, trimethylsilylmethyl, trimethylsilyl, phenyl, naphthyl, allyl, benzyl;
$Ar^2$ is a phenyl group substituted in the 2 and 6 positions by 2° hydrocarbons, 2° substituted hydrocarbons, 3° hydrocarbons, 3° substituted hydrocarbons, or arenes;
Me is methyl.

Preferred non-limiting examples of $Ar^2$ include:

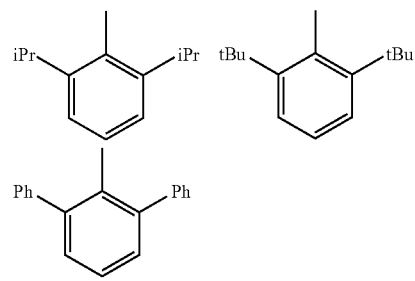

For purposes of this invention, where the terms 2° and 3° are used we mean that the hydrocarbon is 2° or 3° prior to substitution onto the arene ring. For example in the structures above the iPr is 2° and the tBu is 3°.

$Ar^3$ is an arene. Preferred non-limiting examples of $Ar^3$ include:

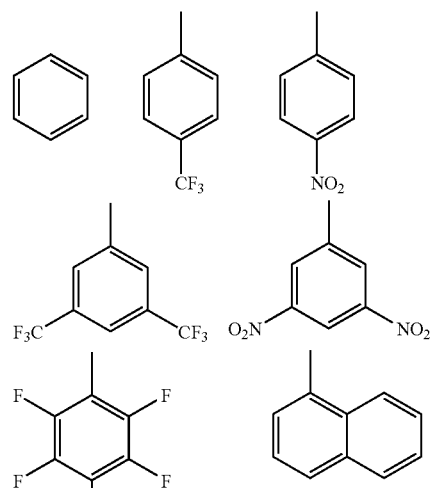

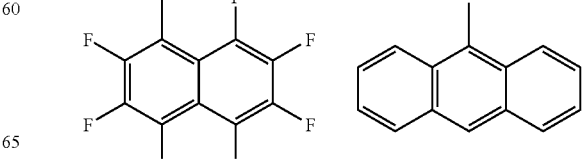

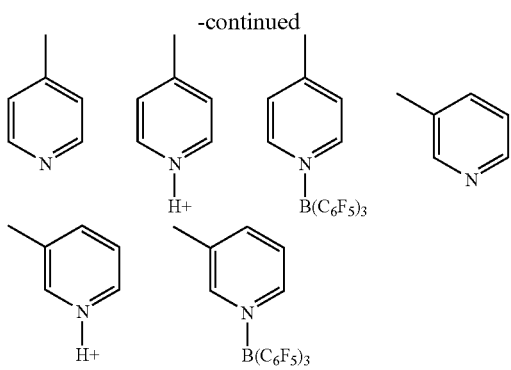

In another preferred embodiment the catalyst compounds described herein may be used in combination with other polymerization and or oligomerization catalysts. In a preferred embodiment the instant catalyst compounds are used in combination with catalyst compounds described in any of the following references:
1. Younkin, T. R.; Connor, E. F.; Henderson, J. I.; Friederich, S. K.; Grubbs, R. H.; Bansleben, D. A. Science 2000, 287, 460
2. Wang, C. Friederich, S.; Younkin, T. R.; Li, R. T.; Grubbs, R. H.; Bansleben, D. A.; Day, M. W. *Organometallics* 1998, 17, 3149.
3. Johnson, L. K.; Bennett, A. M. A.; Wang, L.; Parthasarathy, A.; Hauptman, E.; Simpson, R. D.; Feldman, J.; Coughlin, E. B. WO 98/30609
4. Bansleben, D. A.; Friederich, S. K.; Younkin, T. R.; Grubbs, R. H.; Wang, C.; Li, R. T. WO 98/42664
5. Bansleben, D. A.; Friederich, S. K.; Younkin, T. R.; Grubbs, R. H.; Wang, C.; Li, R. T. WO 98/42665
6. Bansleben, D. A.; Connor, E. F.; Grubbs, R. H.; Henderson, J. I.; Younkin, T. R.; Nadjadi, A. R. WO 2000/56786
7. Bansleben, D. A.; Connor, E. F.; Grubbs, R. H.; Henderson, J. I.; Younkin, T. R.; Nadjadi, A. R. WO 2000/56787
8. Bansleben, D. A.; Friedrich, S. K.; Grubbs, R. H.; Li, R. T.; Connor, E. F.; Roberts, W. P. Wo 2000/56781
9. Hicks, F.; Brookhart, M. *Organometallics* 2001, 20, 3217
10. Connor, E. F.; Younkin, T. R.; Henderson, J. I.; Hwang, S.; Grubbs, R. H.; Roberts, W. P.; Litzau, J. J. *J. Pol. Sci. A*. 2002, 40, 2842
11. Schroeder, D. L.; Keim, w.; Zuideveld, M. A.; Mecking, S, *Macromolecules*, 2002, 35, 6071
12. Matsui, S.; Nitabaru, M.; Tsuru, K.; Fujita, T.; Suzuki, Y.; Takagi, Y.; Tanaka, H. EP 0 990 664 A1
13. Laali, K.; Szele, I.; Zollinger, H., *Helvetica Chimica Acta* 1983, 66, 1737
14. Petrillo, G.; Novi, M.; Garbarino, G.; Filiberti, M., *Tetrahedron* 1989, 45, 7411
15. WO 98/30609
16. Grubbs (Science 2000, 287, 460; *Organometallics* 1998, 17, 3149; *J Pol. Sci. A*. 2002, 40, 2842)
17. WO 98/42665
18. WO 2000/56786
19. WO 2000/56787
20. WO 2000/56781
21. WO 98/30609.

Activators and Activation Methods for Catalyst Compounds

An activator is defined as any combination of reagents that increases the rate at which a metal compound, containing at least one E-Phenoxide ligand and one formal neutral ligand, oligomerizes or polymerizes unsaturated monomers, such as olefins. An activator may also affect the molecular weight, degree of branching, comonomer content, or other properties of the oligomer or polymer. The E-phenoxide compounds according to the invention may be activated for oligomerization and or polymerization catalysis in any manner sufficient to allow coordination or cationic oligomerization and or coordination or cationic polymerization.

Generally speaking, successful olefin oligomerization and/or polymerization catalysts contain a formal anionic ligand, such as hydride or hydrocarbyl, with an adjacent (cis) coordination site accessible to an unsaturated monomer. Coordination of an unsaturated monomer to the cis coordination site allows a migratory insertion reaction to form a metal alkyl. Repetition of this process causes chain growth. An activator is thus any combination of reagents that facilitates formation of a transition metal compound containing, in addition to at least one E-phenoxide ligand, cis coordinated olefin and hydride or hydrocarbyl.

When the E-phenoxide compound contains at least one hydride or hydrocarbyl ligand, activation can be achieved by removal of formal anionic or neutral ligands, of higher binding affinity than the unsaturated monomer. This removal, also called abstraction, process may have a kinetic rate that is first-order or non-first order with respect to the activator. Activators that remove formal anonic ligands are termed ionizing activators. Activators that remove formal neutral ligands are termed non-ionizing activators. Activators are typically strong Lewis-acids which may play either the role of ionizing or non-ionizing activator.

When the E-phenoxide compound does not contain at least one hydride or hydrocarbyl ligands, then activation may be a one step or multi step process. A step in this process includes coordinating a hydride or hydrocarbyl group to the metal compound. A separate activation step is removal of formal anionic or neutral ligands of higher binding affinity than the unsaturated monomer. These activation steps may occur in series or in parallel. These steps may occur in the presence of olefin. These steps may occur prior to exposure to olefin. More than one sequence of activation steps is possible to achieve activation.

The activator may also act to coordinate a hydride or hydrocarbyl group to the metal compound, containing at least one E-Phenoxide ligand and one formal neutral ligand. When the E-phenoxide compound does not contain at least one hydride or hydrocarbyl ligands but does contain at least one functional group ligand, activation may be effected by substitution of the functional group with a hydride, hydrocarbyl or substituted hydrocarbyl group. This substitution may be effected with appropriate hydride or alkyl reagents of group 1, 2, 12, 13 elements as is known in the art. To achieve activation, it may be necessary to also remove formal anionic or neutral ligands of higher binding affinity than the unsaturated monomer.

Alumoxane and aluminum alkyl activators are capable of alkylation and abstraction activation.

The activator may also act to coordinate a hydride or hydrocarbyl group to the metal compound, containing at least one E-Phenoxide ligand and one formal neutral ligand. If the E-phenoxide compound does not contain formal anionic ligands, then a hydride, hydrocarbyl or substituted hydrocarbyl may be coordinated to a metal using electrophilic proton or alkyl transfer reagents represented by $H^+(LB)_nA^-$, $(R^9)^+(LB)_nA^-$. $R^9$ is a hydrocarbyl or a substituted hydrocarbyl; LB is a Lewis-base, n=0, 1 or 2. Non-limiting examples of preferred Lewis-bases are diethyl ether, dimethyl ether, ethanol, methanol, water, acetonitrile, N,N-dimethylaniline. $A^-$ is an anion preferably a substituted hydrocarbon, a functional group, or a non-coordinating anion. Non-limiting examples of A⁻ include halides, carboxylates, phosphates, sulfates, sulfonates, borates, aluminates, alkoxides, thioalkoxides, anionic substituted hydrocarbons, anionic metal complexes.

A. Alumoxane and Aluminum Alkyl Activators

In one embodiment, one or more alumoxanes are utilized as an activator in the catalyst composition of the invention. Alumoxanes, sometimes called aluminoxanes in the art, are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide. Mixtures of different alumoxanes and modified alumoxanes may also be used. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP0 279 586B1, EP0 516 476A, EP0 594 218A1 and WO94/10180.

When the activator is an alumoxane (modified or unmodified), some embodiments select the maximum amount of activator at a 5000-fold molar excess Al/M over the catalyst precursor (per metal catalytic site). The minimum activator-to-catalyst-precursor is typically a 1:1 molar ratio.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. It may be preferable to use a visually clear methylalumoxane. A cloudy or gelled alumoxane can be filtered to produce a clear solution or clear alumoxane can be decanted from the cloudy solution. Another preferred alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum and the like.

B. Ionizing Activators

It is within the scope of this invention to use an ionizing or stoichiometric activator, neutral or ionic, such as tri (n-butyl) ammonium tetrakis (pentafluorophenyl) boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Preferred activators include a cation and an anion component, and may be represented by the following formula:

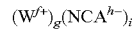

$(W^{f+})_g(NCA^{h-})_i$ $W^{f+}$ is a cation component having the charge f+
$NCA^{h-}$ is a non-coordinating anion having the charge h−
f is an integer from 1 to 3.
h is an integer from 1 to 3.
g and h are constrained by the relationship: $(g)\times(f)=(h)\times(i)$.

The cation component, $(W^{f+})$ may include Bronsted acids such as protons or protonated Lewis bases or reducible Lewis acids capable of protonating or abstracting a moiety, such as an akyl or aryl, from an analogous metallocene or Group 15 containing transition metal catalyst precursor, resulting in a cationic transition metal species.

In a preferred embodiment, the activators include a cation and an anion component, and may be represented by the following formula:

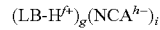

$(LB-H^{f+})_g(NCA^{h-})_i$ wherein LB is a neutral Lewis base;
H is hydrogen;
$NCA^{h-}$ is a non-coordinating anion having the charge h−
f is an integer from 1 to 3,
h is an integer from 1 to 3,
g and h are constrained by the relationship: $(g)\times(f)=(h)\times(i)$.

The activating cation $(W^{f+})$ may be a Bronsted acid, $(LB-H^{f+})$, capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene and mixtures thereof.

The activating cation ($W^{f+}$) may also be an abstracting moiety such as silver, carboniums, tropylium, carbeniums, ferroceniums and mixtures, preferably carboniums and ferroceniums. Most preferably ($W^{f+}$) is triphenyl carbonium or N, N-dimethylanilinium.

The anion component ($NCA^{h-}$) includes those having the formula $[T^{j+}Qk]^{h-}$ wherein j is an integer from 1 to 3; k is an integer from 2 to 6; k−j=h; T is an element selected from Group 13 or 15 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable ($NCA^{h-}$) also include diboron compounds as disclosed in U.S. Pat. No. 5,447,895, which is fully incorporated herein by reference.

Additional suitable anions are known in the art and will be suitable for use with the catalysts of the invention. See in particular, U.S. Pat. No. 5,278,119 and the review articles by S. H. Strauss, "The Search for Larger and More Weakly Coordinating Anions", Chem. Rev., 93, 927–942 (1993) and C. A. Reed, "Carboranes: A New Class of Weakly Coordinating Anions for Strong Electrophiles, Oxidants and Superacids", Acc. Chem. Res., 31, 133–139 (1998).

Illustrative, but not limiting examples of boron compounds which may be used as an activating cocatalyst in the preparation of the improved catalysts of this invention are tri-substituted ammonium salts such as:
trimethylammonium tetraphenylborate,
triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
N,N-dimethyl-(2,4,6-trimethylanilinium)tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl-(2,4,6-trimethylanilinium)tetrakis(pentafluorophenyl)borate,
trimethylammonium tetrakis-(2,3,4,6-tetrafluorophenylborate,
triethylammonium tetrakis-(2,3,4,6-tetrafluorophenyl)borate,
tripropylammonium tetrakis-(2,3,4,6-tetrafluorophenyl)borate,
tri(n-butyl)ammonium tetrakis-(2,3,4,6-tetrafluoro-phenyl)borate,
dimethyl(t-butyl)ammonium tetrakis-(2,3,4,6-tetrafluorophenyl)borate,
N,N-dimethylanilinium tetrakis-(2,3,4,6-tetrafluorophenyl)borate,
N,N-diethylanilinium tetrakis-(2,3,4,6-tetrafluoro-phenyl)borate, and
N,N-dimethyl-(2,4,6-trimethylanilinium)tetrakis-(2,3,4,6-tetrafluorophenyl)borate;
dialkyl ammonium salts such as: di-(i-propyl)ammonium tetrakis(pentafluorophenyl)borate, and dicyclohexylammonium tetrakis(pentafluorophenyl)borate; and tri-substituted phosphonium salts such as: triphenylphosphonium tetrakis(pentafluorophenyl)borate, tri(o-tolyl)phosphonium tetrakis(pentafluorophenyl)borate, and tri(2,6-dimethylphenyl)phosphonium tetrakis(pentafluorophenyl)borate.

Most preferably, the ionic stoichiometric activator is N,N-dimethylanilinium tetra(perfluorophenyl)borate and/or triphenylcarbenium tetra(perfluorophenyl)borate.

In one embodiment, activation methods using ionizing ionic compounds not containing an active proton but capable of producing an analogous metallocene catalyst cation and their non-coordinating anion are also contemplated and are described in EP-A-0 426 637, EP-A-0 573 403 and U.S. Pat. No. 5,387,568, which are all herein incorporated by reference.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Non-coordinating anions useful in accordance with this invention are those that are compatible, stabilize the metal cation in the sense of balancing its ionic charge, yet retain sufficient liability to permit displacement by an ethylenically or acetylenically unsaturated monomer during polymerization. These types of cocatalysts sometimes use tri-isobutyl aluminum or tri-octyl aluminum as a scavenger.

Invention process also can employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", Chem. Rev., 100, 1391–1434 (2000).

When the E-phenoxide complex does not contain at least one hydride or hydrocarbyl ligand but does contain at least one functional group ligand, such as chloride, amido or alkoxy ligands, and the functional group ligands are not capable of discrete ionizing abstraction with the ionizing, anion pre-cursor compounds, these functional group ligands can be converted via known alkylation reactions with organometallic compounds such as lithium or aluminum hydrides or alkyls, alkylalumoxanes, Grignard reagents, etc. See EP-A-0 500 944, EP-A1-0 570 982 and EP-A1-0 612

768 for analogous processes describing the reaction of alkyl aluminum compounds with analogous dihalide substituted metallocene compounds prior to or with the addition of activating noncoordinating anion precursor compounds.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl) boron can be used with methylalumoxane.

C. Non-ionizing Activators

Activators are typically strong Lewis-acids which may play either the role of ionizing or non-ionizing activator. Activators previously described as ionizing activators may also be used as non-ionizing activators.

Abstraction of formal neutral ligands may be achieved with Lewis acids that display an affinity for the formal neutral ligands. These Lewis acids are typically unsaturated or weakly coordinated. Examples of non-ionizing activators include $R^{10}(R^{11})_3$, where $R^{10}$ is a group 13 element and $R^{11}$ is a hydrogen, a hydrocarbyl, a substituted hydrocarbyl, or a functional group. Typically, $R^{11}$ is an arene or a perfluorinated arene. Non-ionizing activators also include weakly coordinated transition metal compounds such as low valent olefin complexes.

Non-limiting examples of non-ionizing activators include $BMe_3$, $BEt_3$, $B(iBu)_3$, $BPh_3$, $B(C_6F_5)_3$, $AlMe_3$, $AlEt_3$, $Al(iBu)_3$, $AlPh_3$, $B(C_6F_5)_3$alumoxane, $CuCl$, $Ni(1,5$-cyclooctadiene$)_2$.

Additional neutral Lewis-acids are known in the art and will be suitable for abstracting formal neutral ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.*, 100, 1391–1434 (2000).

Preferred non-ionizing activators include $R^{10}(R^{11})_3$, where $R^{10}$ is a group 13 element and $R^{11}$ is a hydrogen, a hydrocarbyl, a substituted hydrocarbyl, or a functional group. Typically, $R^{11}$ is an arene or a perfluorinated arene.

More preferred non-ionizing activators include $B(R^{12})_3$, where $R^{12}$ is a an arene or a perfluorinated arene. Even more preferred non-ionizing activators include $B(C_6H_5)_3$ and $B(C_6F_5)_3$. A particularly preferred non-ionizing activator is $B(C_6F_5)_3$. More preferred activators are ionizing and non-ionizing activators based on perfluoroaryl borane and perfluoroaryl borates such as $PhNMe_2H^+B(C_6F_5)_4^-$, $(C_6H_5)_3C^+B(C_6F_5)_4^-$, and $B(C_6F_5)_3$.

It appears that alumoxane and aluminum alkyl activators may act to reduce molecular weight. While not wishing to be bound by theory, we believe however, that in some embodiments the alumoxane or aluminum alkyl may not affect molecular weight or may even increase it.

In general the combined metal compounds and the activator are combined in ratios of about 1000:1 to about 0.5:1. In a preferred embodiment the metal compounds and the activator are combined in a ratio of about 300:1 to about 1:1, preferably about 150:1 to about 1:1, for boranes, borates, aluminates, etc. the ratio is preferably about 1:1 to about 10:1 and for alkyl aluminum compounds (such as diethylaluminum chloride combined with water) the ratio is preferably about 0.5:1 to about 10:1.

In a preferred embodiment the ratio of the first catalyst to the second or additional catalyst is 5:95 to 95:5, preferably 25:75 to 75:25, even more preferably 40:60 to 60:40.

In another embodiment the catalyst compositions of this invention include a support material or carrier. For example, the one or more catalyst components and/or one or more activators may be deposited on, contacted with, vaporized with, bonded to, or incorporated within, adsorbed or absorbed in, or on, one or more supports or carriers.

The support material is any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, which may or may not be dehydrated, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the support material is in the range of from about 50 to about 500 $m^2/g$, pore volume of from about 0.5 to about 3.5 cc/g and average particle size of from about 10 to about 200 μm. Most preferably the surface area of the support material is in the range is from about 100 to about 400 $m^2/g$, pore volume from about 0.8 to about 3.0 cc/g and average particle size is from about 5 to about 100 μm. The average pore size of the carrier of the invention typically has pore size in the range of from 10 to 1000 Å, preferably 50 to about 500 Å, and most preferably 75 to about 350 Å.

Monomers

In a preferred embodiment the catalyst compounds of this invention are used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methyl-pentene-1, 3-methyl pentene-1, 3,5,5-trimethyl hexene 1, and 5-ethyl-1-nonene.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, vinylnorbornene, ethylidene norbornene, cyclopentadiene, cyclopentene, cyclohexene, cyclobutene, vinyladamantane and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Non-limiting examples of preferred polar unsaturated monomers useful in this invention include 6-nitro-1-hexene, N-methylallylamine, N-allylcyclopentylamine, N-allylhexylamine, methyl vinyl ketone, ethyl vinyl ketone, 5-hexen-2-one, 2-acetyl-5-norbomene, 7-syn methoxymethyl-5-norbornen-2-one, acrolein, 2,2-dimethyl-4-pentenal, undecylenic aldehyde, 2,4-dimethyl-2,6-heptadienal, acrylic acid, vinylacetic acid, 4-pentenoic acid, 2,2-dimethyl-4-pentenoic acid, 6-heptenoic acid, trans-2,4-pentadienoic acid, 2,6-heptadienoic acid, nona-fluoro-1-hexene, allyl alcohol, 7-octene-1,2-diol, 2-methyl-3-buten-1-ol, 5-norbornene-2-carbonitrile, 5-norbornene-2-carboxaldehyde, 5-norbornene-2-carboxylic acid, cis-5-norbornene-endo-2,3-dicarboxylic acid, 5-norbornene-2,2,-dimethanol, cis-5-norbornene-endo-2,3-dicarboxylic anhydride, 5-norbornene-2-endo-3-endo-dimethanol, 5-norbornene-2-endo-3-exo-dimethanol, 5-norbornene-2-methanol, 5-norbornene-2-ol, 5-norbornene-2-yl acetate, 1-[2-(5-norbornene-2-yl) ethyl]-3,5,7,9,11,13,15-heptacyclopentylpentacyclo [$9.5.1.1^{3,9}.1^{5,15}.1^{7,13}$]octasiloxane, 2-benzoyl-5-norbornene, allyl 1,1,2,2,-tetrafluoroethyl ether, acrolein dimethyl acetal, butadiene monoxide, 1,2-epoxy-7-octene, 1,2-epoxy-9-decene, 1,2-epoxy-5-hexene, 2-methyl-2-vinyloxirane, allyl glycidyl ether, 2,5-dihydrofuran, 2-cyclopenten-1-one ethylene ketal, allyl disulfide, ethyl acrylate, methyl acrylate.

For purposes of this disclosure, the term oligomer refers to compositions having 2–75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha, omega-dienes are used alone or in combination with mono-alpha olefins.

In a preferred embodiment the process described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of ethylene or a homopolymer of propylene. In another embodiment the polymer is a copolymer comprising ethylene and one or more of any of the monomers listed above. In another embodiment the polymer is a copolymer comprising propylene and one or more of any of the monomers listed above. In another preferred embodiment the copolymers comprises one or more diolefin comonomers, preferably one or more $C_2$ to $C_{40}$ diolefins.

In another preferred embodiment the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably the polymer produced herein is a copolymer of ethylene and one or more of propylene, butene, pentene, hexene, heptene, octene, nonene, decene, dodecene, 4-methyl-pentene-1, 3-methyl pentene-1, and 3,5,5-trimethyl hexene 1.

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methyl-pentene-1, 3-methyl pentene-1, and 3,5, 5-trimethyl hexene 1.

In a preferred embodiment the copolymers described herein comprise at least 50 mole % of a first monomer and up to 50 mole % of other monomers.

In another embodiment, the polymer comprises:
a first monomer present at from 40 to 95 mole %, preferably 50 to 90 mole %, preferably 60 to 80 mole %, and
a comonomer present at from 5 to 60 mole %, preferably 10 to 40 mole %, more preferably 20 to 40 mole %, and
a termonomer present at from 0 to 10 mole %, more preferably from 0.5 to 5 mole %, more preferably 1 to 3 mole %.

In a preferred embodiment the first monomer comprises one or more of any $C_3$ to $C_8$ linear branched or cyclic alpha-olefins, including propylene, butene, (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, cyclohexene, cyclooctene, hexadiene, cyclohexadiene and the like.

In a preferred embodiment the comonomer comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, un-decene, do-decene, hexadecene, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, and cyclohexene.

In a preferred embodiment the termonomer comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, un-decene, do-decene, hexadecene, butadiene, hexadiene, heptadiene, pentadiene, octadiene, nonadiene, decadiene, dodecadiene, styrene, 3,5,5-trimethyl hexene-1, 3-methylpentene-1, 4-methylpentene-1, cyclopentadiene, and cyclohexene.

In a preferred embodiment the polymers described above further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Oligomerization Processes

The catalyst compositions described above may be used to oligomerize or polymerize any unsaturated monomer, however they are preferably used to oligomerize olefins, typically alpha-olefins. In the instant oligomerization processes, the process temperature may be −100° C. to 300° C., −20° C. to 200° C., or 0° C. to 150° C. Some embodiments select oligomerization pressures (gauge) from 0 kPa–35 MPa or 500 kPa–15 MPa. In a preferred embodiment, conditions that favor oligomer production include using aluminum alkyls (as activator or scavenger, etc.) and/or selecting a nickel catalyst compound where $Ar^1$ and or $Ar^2$ comprises phenyl and/or mesityl. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha, omega-dienes are used alone or in combination with mono-alpha olefins.

Preferred oligomerization processes may be run in the presence of various liquids, particularly aprotic organic liquids. Preferably the homogeneous catalyst system, ethylene, alpha-olefins, and product are soluble in these liquids. A supported (heterogeneous) catalyst system may also be used, but will form a slurry rather than a solution. Suitable liquids for both homo- and heterogeneous catalyst systems, include alkanes, alkenes, cycloalkanes, selected halogenated hydrocarbons, aromatic hydrocarbons, and in some cases, hydrofluorocarbons. Useful solvents specifically include hexane, toluene, cyclohexane, and benzene.

The instant invention may also be used to obtain mixtures of alpha-olefins containing desirable numbers of carbon atoms. Factor K from the Schulz-Flory theory (see for instance B. Elvers, et al., Ed. Ullmann's Encyclopedia of Industrial Chemistry, Vol. A13, VCH Verlagsgesellschaft mbH, Weinheim, 1989, p. 243–247 and 275–276) serves as a measure of these α-olefins' molecular weights. From this theory, $K=n(C_{n+2}$ olefin$)/n(C_n$ olefin$)$, where $n(C_n$ olefin$)$ is the number of moles of olefin containing n carbon atoms, and $n(C_{n+2}$ olefin$)$ is the number of moles of olefin containing n+2 carbon atoms, or in other words the next higher oligomer of $C_n$ olefin. From this can be determined the weight (mass) fractions of the various olefins in the resulting product. The ability to vary this factor provides the ability to choose the then-desired olefins.

Invention-made alpha-olefins may be further polymerized with other olefins to form more oligomers or even form homopolymers and copolymers of the alpha olefins produced. These polymers may be made by a number of known methods, such as Ziegler-Natta-type polymerization, metallocene catalyzed polymerization, and other methods, see for instance WO 96/23010, see for instance Angew. Chem., Int. Ed. Engl., vol. 34, p. 1143–1170 (1995); European Patent Application, 416,815; and U.S. Pat. No. 5,198,401 for information about metallocene-type catalysts, and J. Boor Jr., Ziegler-Natta Catalysts and Polymerizations, Academic Press, New York, 1979 and G. Allen, et al., Ed., Comprehensive Polymer Science, Vol. 4, Pergamon Press, Oxford, 1989, pp. 1–108, 409–412 and 533–584, for information about Ziegler-Natta-type catalysts, and H. Mark, et al., Ed., Encyclopedia of Polymer Science and Engineering, Vol. 6, John Wiley & Sons, New York, 1992, p. 383–522, for information about polyethylene.

Preferred oligomerization processes include oligomerizing ethylene to $C_4$–$C_{26}$ linear alpha-olefins.

Oligomers produced herein may be used as polyolefin feed stocks. They may be used as a mixture of olefins alone, as a mixture of olefins added to other olefins, or they may be separated into fractions and then used alone or in combination with other olefins to form polyolefins. Additionally, alpha-olefins produced herein may be converted to alcohols by known processes, these alcohols being useful for a variety of applications such as intermediates for detergents or plasticizers. Typical processes for the conversion of alpha-olefins to alcohols include, but are not limited to the oxo process followed by hydrogenation, or by a modified, single-step oxo process (the modified Shell process), see for instance B. Elvers, et al., Ed., Ullmann's Encyclopedia of Chemical Technology, 5th Ed., Vol. A18, VCH Verlagsgesellschaft mbH, Weinheim, 1991, p. 321–327.

Polymerization Processes

Typically one or more E-phenoxide compounds, one or more activators, and one or more monomers are contacted to produce polymer. The components may be contacted in a solution, bulk, gas or slurry polymerization process or a combination thereof, preferably solution phase or bulk phase polymerization process.

In general the combined E-phenoxide compounds and the activator are combined in ratios of about 1:10,000 to about 1:1, in other embodiments the combined E-phenoxide compounds and the activator are combined in ratios of 1:1 to 100:1. When alumoxane or aluminum alkyl activators are used, the combined pre-catalyst-to-activator molar ratio is from 1:5000 to 10:1, alternatively from 1:1000 to 10:1; alternatively, 1:500 to 2:1; or 1:300 to 1:1. When ionizing activators are used, the combined pre-catalyst-to-activator molar ratio is from 10:1 to 1:10; 5:1 to 1:5; 2:1 to 1:2; or 1.2:1 to 1:1. Multiple activators may be used, including using mixtures of alumoxanes or aluminum alkyls with ionizing activators.

One or more reactors in series or in parallel may be used in the present invention. Catalyst component and activator may be delivered as a solution or slurry, either separately to the reactor, activated in-line just prior to the reactor, or preactivated and pumped as an activated solution or slurry to the reactor. A preferred operation is two solutions activated in-line. Polymerizations are carried out in either single reactor operation, in which monomer, comonomers, catalyst/activator, scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors.

Ethylene-alpha-olefin (including ethylene-cyclic olefin and ethylene-alpha-olefin-diolefin) elastomers of high molecular weight and low crystallinity can be prepared utilizing the catalysts of the invention under traditional solution processes or by introducing ethylene gas into a slurry utilizing the alpha-olefin or cyclic olefin or mixture thereof with other monomers, polymerizable and not, as a polymerization diluent in which the catalyst suspension is suspended. Typical ethylene pressures will be between 10 and 1000 psig (69–6895 kPa) and the polymerization diluent temperature will typically be between –10 and 160° C. The process can be carried out in a stirred tank reactor or a tubular reactor, or more than one reactor operated in series or in parallel. See the general disclosure of U.S. Pat. No. 5,001,205 for general process conditions. All documents are incorporated by reference for description of polymerization processes, ionic activators and useful scavenging compounds.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to about 110° C., and most preferably in the range of from about 70° C. to about 95° C. In another embodiment when high density polyethylene is desired then the reactor temperature is typically between 70 and 105° C.

The productivity of the catalyst or catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

In another preferred embodiment the catalyst system in is liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

Slurry Phase Polymerization

A slurry polymerization process generally operates between 1 to about 50 atmosphere pressure range (15 psi to 735 psi, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Another process of the invention is where the process, preferably a slurry or gas phase process is operated in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-isobutyl aluminum and an excess of alumoxane or modified alumoxane.

Homogeneous, Bulk or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10–30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1–16,000 MPa), most preferably from 1.0 to 500 bar (10–5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor or plug flow reactor, or more than one reactor operated in series or parallel. These reactors may have or may not have internal cooling and the monomer feed my or may not be refrigerated. See the general disclosure of U.S. Pat. No. 5,001,205 for general process conditions. See also, international application WO 96/33227 and WO 97/22639.

Additional embodiments in multiple dependent format include:

1. A composition represented by the formula:

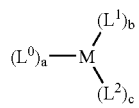

wherein

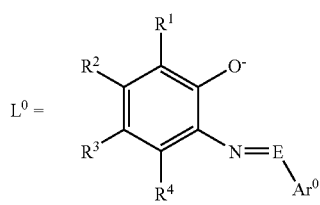

M is selected from groups 3–11 of the periodic table;
E is nitrogen or phosphorus;
$Ar^0$ is arene;
$R^1$–$R^4$ are, each independently, selected from hydrogen, hydrocarbyl, substituted hydrocarbyl or functional group, provided however that $R^3$ and $R^4$ do not form a naphthyl ring;
$L^1$ represents a formal anionic ligand,
$L^2$ represents a formal neutral ligand,
a is an integer greater than or equal to 1;
b is an integer greater than or equal to 0; and
c is an integer greater than or equal to 1.

2. The composition of paragraph 1 wherein M is a group 4 or 10 metal.
3. The composition of paragraph 1 wherein M is titanium and or nickel.
4. The composition of any of paragraphs 1, 2 or 3 wherein E is nitrogen.
5. The composition of any of paragraphs 1, 2, 3 or 4 wherein a is 1, 2, 3, or 4.
6. The composition of any of paragraphs 1, 2, 3, 4 or 5 wherein a is 1 or 2.
7. The composition of any of paragraphs 1, 2, 3, 4, 5 or 6 where b is 0, 1 or 2 and c is 1 or 2.
8. The composition of any of paragraphs 1, 2, 3, 4, 5, 6, or 7 wherein Ar comprises one or more arenes selected from the group consisting of ZETA-ARENES.
9. The composition of any of paragraphs 1, 2, 3, 4, 5, 6, 7 or 8 further comprising an activator.
10. The composition of any of paragraphs 1, 2, 3, 4, 5, 6, 7, 8 or 9 wherein
   $L^2$ is selected from the group consisting of ethers, ketones, esters, alcohols, carboxylic acids, amines, imines, azo, nitrites, heterocycles, phosphines, thioethers, alkyls, alkenes, alkynes, arenes and combinations thereof; and
   $L^1$ is selected from the group consisting of hydrides, fluorides, chlorides, bromides iodides, alkyls, aryls, alkenyls alkynyls, allyls, benzyls, acyls, trimethylsilyls or combinations thereof;
   Ar is selected from the group consisting of substituted or unsubstituted heterocyclics, polyheterocyclics, heterocyclic ring assemblies, fused heterocyclic ring systems or combinations thereof.

11. The composition of any of paragraphs 1, 2, 3, 4, 5, 6, 7, 8, or 9 wherein $L^1$ is selected from the group consisting of ZETA-FORMAL ANIONIC LIGANDS, and $L^2$ is selected from the group consisting of ZETA-FORMAL NEUTRAL LIGANDS.
12. The composition of any of paragraphs 1, 2, 3, 4, 5, 6, 7, 8, 9, 10 or 11 wherein $L^1$ is selected from the group consisting of —F, —Cl, —Br, —I, —N(CH$_3$)$_2$, —OCH$_3$, —H, —CH$_3$, —C$_6$H$_5$, -Allyl, -Benzyl, —CH$_2$Si(CH$_3$)$_3$.
13. A process to oligomerize unsaturated monomers comprising combining monomer, activator and the composition of any of paragraphs 1–12 or claims 16–29 below.
14. A process to polymerize olefins comprising combining olefins, activator and the composition of any of paragraphs 1–12 or claims 16–29 below.
15. A process to oligomerize unsaturated monomers comprising combining monomer and the composition of any of paragraphs 1–12 or claims 16–29 below.
16. A process to polymerize olefins comprising combining olefins and the composition of any of paragraphs 1–12 or claims 16–29 below.

Polymers Produced

The polymers produced herein, particularly the ethylene homopolymers and copolymers, may have a weight average molecular weight (Mw) of 25,000 to 500,000. The polymers produced herein, particularly the ethylene homopolymers and copolymers, may have a molecular weight distribution (Mw/Mn) of up to 5, more preferably of up to 4 more preferably from 1.1 to 3, more preferably from 1.1 to 2.

Any of the polymers or oligomers produced by this invention, may be functionalized after polymerization or oligomerization. Preferred functional groups include maleic acid and maleic anhydride. By functionalized is meant that the polymer has been contacted with an unsaturated acid or anhydride. Preferred unsaturated acids or anhydrides include any unsaturated organic compound containing at least one double bond and at least one carbonyl group. Representative acids include carboxylic acids, anhydrides, esters and their salts, both metallic and non-metallic. Preferably the organic compound contains an ethylenic unsaturation conjugated with a carbonyl group (—C=O). Examples include maleic, fumaric, acrylic, methacrylic, itaconic, crotonic, alpha-methyl crotonic, and cinnamic acids as well as their anhydrides, esters and salt derivatives. Maleic anhydride is particularly preferred. The unsaturated acid or anhydride is preferably present at about 0.1 weight % to about 10 weight %, preferably at about 0.5 weight % to about 7 weight %, even more preferably at about 1 to about 4 weight % based upon the weight of the hydrocarbon resin and the unsaturated acid or anhydride.

EXAMPLES

In the following examples:

Molecular weights (weight average molecular weight (Mw) and number average molecular weight (Mn)) are determined using high throughput measurement techniques such as those disclosed in U.S. Pat No. 6,475,391.

The precatalyst compounds used in the following examples are represented by the formulae below:

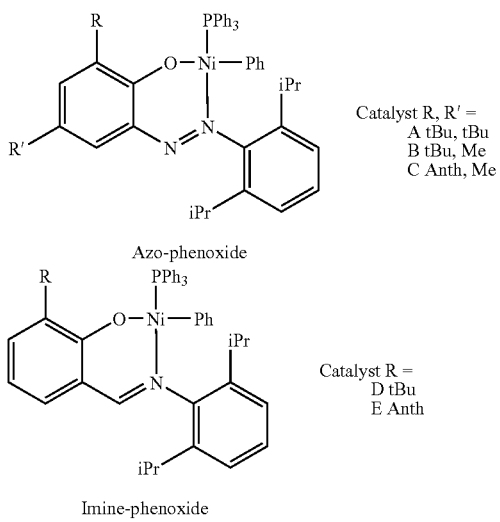

where Ph is phenyl, Me is methyl, Pr is propyl, iPr is isopropyl, tBu is t-butyl, and Anth is anthracenyl.

Ortho substituted phenols were prepared by literature methods (WO 98/42664) or obtained by commercial suppliers. D and E were prepared according to literature methods (WO 98/42664).

EXAMPLES

Preparation of 2-(2',6'-Diisopropylphenylazo)-4-methyl-6-tertbutylphenol.

A theoretical yield of 7.4 mmol of diazotized 2,6-diisopropylaniline, prepared as reported (*Helvetica Chimica Acta* 1983, 66, 1737), was quenched with a phenolate solution comprised of 2-tertButyl-4-methylphenol (1.07 g), water (15 mL), NaOH (0.5 g), pyridine (3 mL), and toluene (6mL) cooled in an ice bath. The resulting highly colored organic layer was concentrated by solvent evaporation to an oil. The aqueous layer was removed and the oil was chromatographed on silica gel eluted with hexanes. The colored band was collected and upon concentration the azo dye crystallized. Yield=0.81 g (35%).

Preparation of 2-(2',6'-Diisopropylphenylazo)-4,6-ditertbutylphenol.

This phenol was prepared, as described for above, from a theoretical yield of 7.4 mmol of diazotized 2,6-diisopropylaniline and a phenolate solution comprised of 2,4-Ditertbutylphenol (1.42 g), water (15 mL), NaOH (0.5 g), pyridine (3 mL), and toluene (6 mL) Yield=0.98 g (36%).

Preparation of 2-(2',6'-Diisopropylphenylazo)-4-methyl-6-(9-anthracenyl)phenol.

This phenol was prepared, as described above, from a theoretical yield of 3.9 mmol of diazotized 2,6-diisopropylaniline and a phenolate solution comprised of 2-(9-Anthracenyl)-4-methylphenol (0.63 g), water (20 mL), NaOH (20 mmol), pyridine (2 mL), and benzene (4 mL). In this case, the product was eluted with ether:hexanes (1:10). Yield=0.30 g (29%).

Preparation of [2-(2',6'-Diisopropylphenylazo)-4,6-ditertbutylphenoxide]-Nickel(phenyl)(triphenylphosphine) (A).

Benzene (15 mL) was added to a stirred slurry of sodium 2-(2',6'-Diisopropylphenylazo)-4-methyl-6-(9-anthracenyl) phenoxide (150 mg, 0.36 mmol), $(PPh_3)_2Ni(Ph)(Br)$ (237 mg, 0.32 mmol) and hexane (1 mL). After 1.5 h, the solvent was evaporated and the residue treated with hexane to give a precipitate which was isolated then extracted with toluene, filtered and upon standing yielded a brown solid which was isolated, washed with hexane then dried. Yield=120 mg (47% yield).

Preparation of [2-(2',6'-Diisopropylphenylazo)-4-methyl-6-tert-butylphenoxide]-Nickel(phenyl)(triphenylphosphine) (B).

Benzene (15 mL) was added to a stirred slurry of sodium 2-(2',6'-Diisopropylphenylazo)-4-methyl-6-tertbutylphenoxide (175 mg, 0.47 mmol), $(PPh_3)_2Ni(Ph)(Br)$ (310 mg, 0.42 mmol) and hexane (1 mL). After 1.5 h, the solvent was evaporated and the residue extracted with hexane (10 mL). After filtering, the extract was stirred overnight to completely convert the kinetic to the thermodynamic product. The product precipitated out of solution. Yield=200 mg (63% yield).

Preparation of [2-(2',6'-Diisopropylphenylazo)-4-methyl-6-(9-anthracenyl)phenoxide]-Nickel(phenyl)(triphenylphosphine) (C).

$(PPh_3)_2Ni(Ph)(Br)$ (560 mg, 0.76 mmol) was added to a solution of potassium 2-(2',6'-Diisopropylphenylazo)-4-methyl-6-(9-anthracenyl)phenoxide (0.56 mmol) and THF (45 mL). The color changed to red/brown. After 2 h, the solvent was removed and the residue extracted with pentane (70 mL), filtered then dried. Residual phosphine was removed by trituration with pentane, overnight at −30° C., to give the product as the remaining dark red/brown powder. Yield=310 mg (64%).

Polymerizations

Polymerizations were conducted in autoclaves lined with glass test tubes (internal volume of reactor=23.5 mL). A solution of precatalyst and toluene were added to a mixture of toluene, octene, $B(C_6F_5)_3$ and ethylene in amounts given in Tables 1, 2, 3, 4, and A. Ethylene was allowed to flow into the autoclaves during polymerization. Polymerizations were halted by addition of an $O_2$/Ar gas mixture to the cells. The reactors were then vented and cooled. Polymer was isolated after the solvent was removed in-vacuo. Molecular weights were determined by GPC relative to polystyrene standards. Comonomer content was determined by IR spectroscopy as described earlier. Unless otherwise indicated activity is reported as g pol/mmol cat h.

TABLE A

Monomer Feed Conditions for Tables 1 to 4.

| Condition | Table 1 | Table 1 | Table 1 | Tables 2 & 4 | Table 4 | Table 3 | Table 3 | Table 3 |
|---|---|---|---|---|---|---|---|---|
| Temperature (° C.) | 40 | 40 | 40 | 40 | 75 | 40 | 40 | 40 |
| octene (mL) | 0 | 0 | 0 | 0 | 0 | 1 | 1 | .2 |

TABLE A-continued

Monomer Feed Conditions for Tables 1 to 4.

| Condition | Table 1 | Table 1 | Table 1 | Tables 2 & 4 | Table 4 | Table 3 | Table 3 | Table 3 |
|---|---|---|---|---|---|---|---|---|
| toluene (mL) | 5.7734 | 5.541 | 5.304 | 5.1491 | 5.2243 | 4.7734 | 4.541 | 5.104 |
| ethylene pressure (psig) | 41 | 120 | 207 | 264 | 264 | 41 | 120 | 207 |
| [ethylene] (mol/L) | .44 | 1.11 | 1.86 | 2.35 | 1.49 | .447 | 1.12 | 1.87 |
| [octene] (mol/L) | 0 | 0 | 0 | 0 | 0 | 1.06 | 1.06 | .21 |
| [ethylene]/[ocetene] | NA | NA | NA | NA | NA | .422 | 1.06 | 8.91 |

TABLE 1

Ethylene Polymerization vs. Ethylene Pressure (Polymerization temperature 40° C., 0 mol % octene, 2 equivalents of $B(C_6F_5)_3$).

| Ex. | Precatalyst 0.8 μmol | Ethylene (psig) | Activity | Yield (mg) | Branch (mol %) | Mw | Mw/Mn |
|---|---|---|---|---|---|---|---|
| 39 | B | 41.1 | 158 | 31 | 7.7 | 55,400 | 1.5 |
| 40 | B | 41.1 | 164 | 32 | 7.7 | 57,100 | 1.5 |
| 51 | C | 41.1 | 188 | 32 | 1.3 | 237,000 | 1.7 |
| 52 | C | 41.1 | 180 | 32 | 1.0 | 238,000 | 1.7 |
| 63 | E | 41.1 | 702 | 49 | 4.5 | 129,000 | 1.6 |
| 64 | E | 41.1 | 650 | 48 | 4.5 | 128,000 | 1.6 |
| 75 | D | 41.1 | 58 | 22 | 0.51 | 16,000 | 1.5 |
| 76 | D | 41.1 | 86 | 26 | 8.9 | 18,000 | 1.5 |
| 41 | B | 120.1 | 333 | 27 | 7.3 | 75,700 | 1.5 |
| 42 | B | 120.1 | 325 | 25 | 6.6 | 79,700 | 1.5 |
| 53 | C | 120.1 | 681 | 38 | 1.3 | 314,000 | 1.6 |
| 54 | C | 120.1 | 651 | 37 | 1.0 | 300,000 | 1.6 |
| 65 | E | 120.1 | 1593 | 59 | 2.4 | 220,000 | 1.5 |
| 66 | E | 120.1 | 1533 | 58 | 2.4 | 220,000 | 1.6 |
| 77 | D | 120.1 | 186 | 17 | 9.3 | 24,000 | 1.9 |
| 78 | D | 120.1 | 184 | 14 | a | a | a |
| 43 | B | 207.4 | 658 | 34 | 6.9 | 85,000 | 1.5 |
| 44 | B | 207.4 | 578 | 26 | 6.2 | 83,000 | 1.5 |
| 55 | C | 207.4 | 1214 | 39 | 1.0 | 299,000 | 1.6 |
| 56 | C | 207.4 | 1260 | 46 | 1.3 | 317,000 | 1.6 |
| 67 | E | 207.4 |  | a | a | a | A |
| 68 | E | 207.4 | 2245 | 62 | 2.4 | 261,000 | 1.6 |
| 79 | D | 207.4 | 212 | 10 | a | a | A |
| 80 | D | 207.4 | 202 | 9 | a | a | A |

$^a$not determined

TABLE 2

Ethylene Polymerization vs. Equivalents of $B(C_6F_5)_3$ (Polymerization temperature 40° C., 0 mol % octene, Ethylene pressure 264 psig)

| Ex. | Precatalyst 0.8 μmol | Equiv. $B(C_6F_5)_3$ | Activity | Yield (mg) | Branch (mol %) | Mw | Mw/Mn |
|---|---|---|---|---|---|---|---|
| 87 | B | 0 | 664 | 28 | 5.9 | 89,000 | 1.5 |
| 88 | B | 0 | 727 | 31 | 5.9 | 87,000 | 1.5 |
| 89 | B | 1 | 722 | 25 | 5.5 | 91,000 | 1.5 |
| 90 | B | 1 | 730 | 26 | .3 | 89,000 | 1.5 |
| 91 | B | 5 | 685 | 26 | 5.5 | 85,000 | 1.7 |
| 92 | B | 5 | 625 | 32 | 5.9 | 82,000 | 1.8 |
| 93 | C | 0 | 717 | 33 | 0.8 | 285,000 | 1.6 |
| 94 | C | 0 | 655 | 27 | 0.5 | 246,000 | 1.6 |
| 95 | C | 1 | 1212 | 43 | 0.8 | 332,000 | 1.5 |
| 96 | C | 1 | 1075 | 33 | 0.8 | 301,000 | 1.5 |
| 97 | C | 5 | 2421 | 85 | 1.0 | 332,000 | 1.6 |
| 98 | C | 5 | 2856 | 107 | 1.0 | 329,000 | 1.6 |
| 99 | E | 0 | 1735 | 58 | 1.3 | 274,000 | 1.3 |
| 100 | E | 0 | 1699 | 64 | 1.0 | 302,000 | 1.4 |
| 101 | E | 1 | 2075 | 60 | 1.3 | 297,000 | 1.4 |
| 102 | E | 1 |  | a | a | a |  |
| 103 | E | 5 | 2937 | 84 | 1.6 | 270,000 | 1.6 |
| 104 | E | 5 | 2823 | 81 | 1.6 | 280,000 | 1.5 |
| 105 | D | 0 | 273 | 16 | 10.5 | 36,000 | 1.5 |
| 106 | D | 0 | 300 | 15 | a | a | a |
| 107 | D | 1 | 240 | 9 | a | a | a |
| 108 | D | 1 | 214 | 7 | a | a | a |
| 109 | D | 5 | 194 | 6 | a | a | a |
| 110 | D | 5 | 225 | 7 | a | a | a |

$^a$not determined

TABLE 3

Ethylene Octene Copolymerizations (Polymerization temperature 40° C., 2 equivalents of $B(C_6F_5)_3$.)

| Ex. | Precatalyst 0.8 μmol | Ocetene (mL) | Ethylene (psig) | Activity | Yield (mg) | Octene (mol %) | Mw | Mw/Mn |
|---|---|---|---|---|---|---|---|---|
| 45 | B | 1 | 41.1 | 152 | 31 | 5.6 | 38,700 | 1.5 |
| 46 | B | 1 | 41.1 | 160 | 30 | 5.1 | 40,200 | 1.5 |
| 57 | C | 1 | 41.1 | 245 | 33 | 8.2 | 47,000 | 1.4 |
| 58 | C | 1 | 41.1 | 240 | 35 | 8.6 | 45,000 | 1.5 |
| 69 | E | 1 | 41.1 | 645 | 46 | 5.6 | 30,000 | 1.5 |
| 70 | E | 1 | 41.1 | 619 | 47 | 7.8 | 28,000 | 1.6 |
| 81 | D | 1 | 41.1 | 86 | 22 | a | 14,000 | 1.5 |
| 82 | D | 1 | 41.1 | 77 | 24 | a | 14,000 | 1.5 |
| 47 | B | 1 | 120.1 | 428 | 30 | 3.2 | 52,500 | 1.5 |

TABLE 3-continued

Ethylene Octene Copolymerizations (Polymerization temperature 40° C., 2 equivalents of B(C$_6$F$_5$)$_3$).)

| Ex. | Precatalyst 0.8 μmol | Ocetene (mL) | Ethylene (psig) | Activity | Yield (mg) | Octene (mol %) | Mw | Mw/Mn |
|---|---|---|---|---|---|---|---|---|
| 48 | B | 1 | 120.1 | 426 | 31 | 3.6 | 53,300 | 1.5 |
| 59 | C | 1 | 120.1 | 569 | 27 | 4.1 | 84,000 | 1.6 |
| 60 | C | 1 | 120.1 | 591 | 32 | 3.8 | 86,000 | 1.6 |
| 71 | E | 1 | 120.1 | 1259 | 44 | 3.8 | 61,000 | 1.5 |
| 72 | E | 1 | 120.1 | 1095 | 38 | 4.9 | 60,000 | 1.8 |
| 83 | D | 1 | 120.1 | 188 | 16 | a | 22,000 | 1.5 |
| 84 | D | 1 | 120.1 | 208 | 17 | a | 23,000 | 1.5 |
| 49 | B | 0.2 | 207.4 | 651 | 22 | −0.35 | 79,800 | 1.5 |
| 50 | B | 0.2 | 207.4 | 496 | 13 | a | a | a |
| 61 | C | 0.2 | 207.4 | 1082 | 27 | 0.45 | 231,000 | 1.6 |
| 62 | C | 0.2 | 207.4 | 1088 | 20 | 0.65 | 191,000 | 2.2 |
| 73 | E | 0.2 | 207.4 | 2227 | 58 | −0.3 | 211,000 | 1.5 |
| 74 | E | 0.2 | 207.4 | 2474 | 59 | 2.1 | 207,000 | 1.5 |
| 85 | D | 0.2 | 207.4 | 201 | 6 | a | a | a |
| 86 | D | 0.2 | 207.4 | 209 | 7 | a | a | a |

$^a$not determined

TABLE 4

Precatalyst Concentration Sweep at 40° C. and 75° C. (Ethylene pressure 264 psig, 0 mol % octene, 2 equivalents B(C$_6$F$_5$)$_3$).

| Run | Precat (μmol) | Temp (° C.) | Activity | Yield (mg) | Mw | Mw/Mn |
|---|---|---|---|---|---|---|
| 1 | B - 0.2 | 40 | 4694 | 61 | 109,100 | 1.6 |
| 2 | B - 0.4 | 40 | 510 | 9 | a | A |
| 3 | B - 0.8 | 40 | 4799 | 183 | 94,500 | 1.6 |
| 7 | A - 0.2 | 40 | 4293 | 57 | 128,900 | 1.6 |
| 8 | A - 0.4 | 40 | 278 | 5 | a | A |
| 9 | A - 0.8 | 40 | 6786 | 160 | 116,500 | 1.6 |
| 13 | C - 0.4 | 40 | 3111 | 54 | 352,300 | 1.8 |
| 14 | C - 0.8 | 40 | 7834 | 258 | 433,100 | 1.8 |
| 18 | E - 0.2 | 40 | 1320 | 14 | a | A |
| 19 | E - 0.4 | 40 | 1912 | 30 | 336,000 | 1.6 |
| 20 | E - 0.8 | 40 | 17117 | 469 | 370,800 | 1.9 |
| 23 | D - 0.4 | 40 | 304 | 3 | a | A |
| 24 | D - 0.8 | 40 | 163 | 46 | 38,800 | 1.6 |
| 5 | B - 0.4 | 75 | 988 | 25 | 24,200 | 1.7 |
| 6 | B - 0.8 | 75 | 1218 | 35 | 223,00 | 1.7 |
| 10 | A - 0.2 | 75 | 259 | 11 | a | A |
| 11 | A - 0.4 | 75 | 619 | 28 | 27,500 | 1.7 |
| 12 | A - 0.8 | 75 | 1379 | 40 | 25,800 | 1.7 |
| 15 | C - 0.2 | 75 | 2888 | 27 | 90,800 | 1.7 |
| 16 | C - 0.4 | 75 | 4419 | 52 | 76,600 | 1.8 |
| 17 | C - 0.8 | 75 | 4909 | 78 | 66,600 | 1.6 |
| 21 | E - 0.4 | 75 | 47736 | 314 | 44,400 | 1.9 |
| 22 | E - 0.8 | 75 | 15631 | 157 | 24,600 | 1.9 |
| 25 | D - 0.2 | 75 | 1569 | 2 | a | A |
| 26 | D - 0.4 | 75 | 20 | 8 | a | A |
| 27 | D - 0.8 | 75 | 67 | 12 | a | A |

$^a$not determined

The molecular weight capabilities of the azo- and known imine-phenoxide systems (Science 2000, 287, 460; Organometallics 1998, 17, 3149; WO 98/42664; WO 98/42665; WO 2000/56786; WO 2000/56787; WO 2000/56781) are illustrated graphically in drawings 1, 2 and 3. Drawing 1 reveals that the azo systems containing the 2,6-diisopropylphenyl substituent on nitrogen give higher Mw polyethylene than the analogous imine complexes from 41 to 207 psig ([ethylene]=0.44–1.9 mol/L) at 40° C. At 75° C. the Mw of the anthracenyl substituted azo catalyst system (91, 77, 67 K) are significantly higher than the imine analogue (25, 44 K). As shown in drawing 2, the Mw capability of the azo precatalysts are either comparable or higher than the imine analogues at higher ethylene pressure, 264 psig (2.4 mol/L). The presence of an activator (B(C$_6$F$_5$)$_3$) appears to have a small effect on Mw at this pressure; however, the presence of B(C$_6$F$_5$)$_3$ causes a significant increase in activity (Table 2).

The ability of azo- and known imine-phenoxide systems to copolymerize ethylene and 1-octene were examined. Drawing 3 graphically reveals copolymer Mw versus mol % octene incorporated. The mol % octene incorporated was determined from the difference in response of the methyl bending vibration of branched polyethylene and the ethylene octene copolymers, prepared at the same ethylene concentrations, to IR analysis relative to standard ethylene/octene copolymers. This method thus subtracts out the branch content inherent in the homopolymerization. The branch content in the homopolyethylene estimated by this method decreases with increasing ethylene concentration in solution. The octene incorporation is comparable to that reported by Grubbs in a recent paper (J. Pol. Sci. A. 2002, 40, 2842). Each system shows a clear drop in Mw with octene incorporation however, the anthracenyl substituted azo catalyst system displays higher Mw copolymer for a composition between 4 and 8 mol % octene than the analogous imine-phenoxide system. The branching values and comonomer content reported below were determined by this method.

Very recently an azo-phenoxide precatalyst was reported in the literature by Mecking and coworkers (Macromolecules, 2002, 35, 6071). The Mecking system is shown as complexes F, G and H) and their reported polymerization results are displayed in Table 5. A notable feature of this data is the Mw capability of Mecking's catalyst. After correcting for the difference in measurement (Mw measured vs. PS is ca. 2x that vs. PE), the catalysts reported here still have a significant Mw advantage over Mecking's system (ca. 150 K vs ca 50 K).

TABLE 5

Data Reported in Mecking in Macromolecules, 2002, 35, 6071, for Polymerization and Oligomerization of Ethylene by Complexes F–H. (total volume of toluene 20 mL)

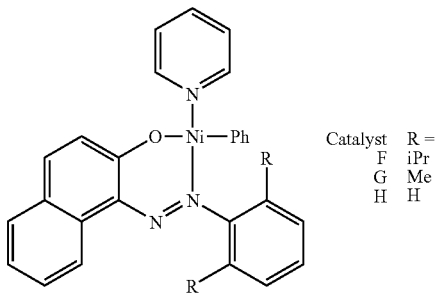

Catalyst  R =
F         iPr
G         Me
H         H

| Ex. | Precat 50 μmol | Temp | Ethylene pressure (bar) | Polym Time (hr) | Product PE = Polyethylene, Olig = oligomer | Productivity | Avg Activity | Mw[A] | Mw/Mn |
|---|---|---|---|---|---|---|---|---|---|
| 1  | F | 50° C. | 50 | 2 | PE | 3180 | 1590 | 45,000 | 2.3 |
| 2  | G | 50° C. | 50 | 1 | olig | 940 | 940 | | |
| 3  | G | 50° C. | 50 | 2 | olig | 1790 | 900 | | |
| 4  | G | 50° C. | 50 | 4 | olig | 2820 | 710 | | |
| 5  | G | 50° C. | 50 | 8 | olig | 2870 | 360 | | |
| 6  | H | 50° C. | 50 | 2 | olig, Cmax 19 | 2550 | 1280 | | |
| 7  | F | 25° C. | 5  | 2 | PE | <10 | <10 | | |
| 8  | F | 25° C. | 20 | 2 | PE | 360 | 180 | 23,000 | 1.8 |
| 9  | F | 25° C. | 50 | 2 | PE | 840 | 420 | 46,000 | 2.3 |
| 10 | F | 70° C. | 50 | 2 | PE | 5710 | 2860 | 52,000 | 1.9 |

[A]Determined from GPC, referenced to linear polyethylene.

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

The invention claimed is:

1. A composition represented by the formula:

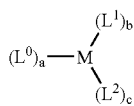

wherein

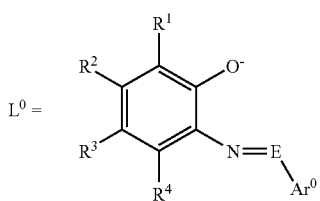

M is selected from groups 3–11 of the periodic table;
E is nitrogen or phosphorus;
$Ar^0$ is arene;

$R^1$–$R^4$ are, each independently, selected from hydrogen, hydrocarbyl, substituted hydrocarbyl or functional group, provided however that $R^3$ and $R^4$ do not form a naphthyl ring;
$L^1$ represents a formal anionic ligand,
$L^2$ represents a formal neutral ligand,
a is an integer greater than or equal to 1;
b is an integer greater than or equal to 0; and
c is an integer greater than or equal to 1.

2. The composition of claim 1 wherein M is a group 4 or 10 metal.

3. The composition of claim 1 wherein M is titanium or nickel.

4. The composition of claim 1 wherein E is nitrogen.

5. The composition of claim 1 wherein a is 1, 2, 3, or 4.

6. The composition of claim 1 wherein a is 1 or 2.

7. The composition of claim 1 wherein b is 0, 1 or 2 and c is 1 or 2.

8. The composition of claim 1 wherein $Ar^0$ is selected from the group consisting of ZETA-ARENES.

9. The composition of claim 1 further comprising an activator.

10. The composition of claim 1 wherein
each $L^2$ is, independently, selected from the group consisting of ethers, ketones, esters, alcohols, carboxylic acids, amines, imines, azo, nitriles, heterocycles, phosphines, thioethers, alkyls, alkenes, alkynes, arenes and combinations thereof; and
each $L^1$ is, independently, selected from the group consisting of hydrides, fluorides, chlorides, bromides, iodides, alkyls, aryls, alkenyls, alkynyls, allyls, benzyls, acyls, trimethylsilyls and combinations thereof;

Ar⁰ is selected from the group consisting of substituted or unsubstituted heterocyclics, polyheterocyclics, heterocyclic ring assemblies, fused heterocyclic ring systems or combinations thereof.

11. The composition of claim 10 wherein M is nickel or titanium.

12. The composition of claim 11 wherein a=1 or 2, b=0, 1 or 2, and c=1 or 2.

13. The composition of claim 10 further comprising an activator.

14. The composition of claim 1 wherein $L^1$ is selected from the group consisting of ZETA-FORMAL ANIONIC LIGANDS, and $L^2$ is selected from the group consisting of ZETA-FORMAL NEUTRAL LIGANDS.

15. The composition of claim 1 wherein $L^1$ is selected from the group consisting of —F, —Cl, —Br, —I, —N(CH₃)₂, —OCH₃, —H, —CH₃, —C₆H₅, -allyl, -benzyl, —CH₂Si(CH₃)₃.

16. A composition represented by one of the following formulae:

| | |
|---|---|
| (L⁰)ₐ(L¹)_{b−2}(L²)_cM(R⁵)₂ <br> 2 | (L⁰)ₐ(L¹)_{b−2}(L²)_cM(R⁵)₁(L³)₁ <br> 3 |
| (L⁰)ₐ(L¹)_{b−2}(L²)_cM(L³)₂ <br> 4 | (L⁰)ₐ(L²)_cM <br> 5 |
| (L⁰)ₐ(L¹)_{b−1}(L²)_cM(R⁵)₁ <br> 6 | (L⁰)ₐ(L¹)_{b−1}(L²)_cM(L³)₁ <br> 7 | wherein:
M is selected from groups 3–11 of the periodic table,
L⁰ represents an E-phenoxide ligand represented by the formula:

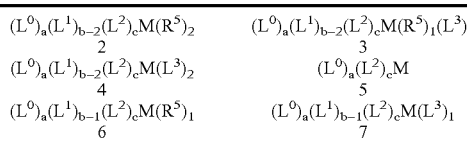

$L^1$ represents a formal anionic ligand;
$L^2$ represents a formal neutral ligand;
$L^3$ represents a formal anionic ligand that comprises a functional group;
a is 1, 2, 3 or 4;
b is 0, 1, 2, 3, 4, 5 or 6, provided that b is not 0 or 1 in formula 2, 3 or 4 and b is not 0 in formula 6 or 7;
c is 1, 2, 3 or 4;
E is nitrogen or phosphorus;
Ar⁰ is an arene selected from the group consisting of ZETA-ARENES;
$R^1$–$R^4$ are each independently hydrogen, a hydrocarbyl, a substituted hydrocarbyl or a functional group, provided that $R^3$ and $R^4$ do not form a naphthyl ring; and
$R^5$ is a hydride, a hydrocarbyl or a substituted hydrocarbyl.

17. The composition of claim 16 wherein E is nitrogen and M is titanium or nickel.

18. A composition represented by one of the following formulae:

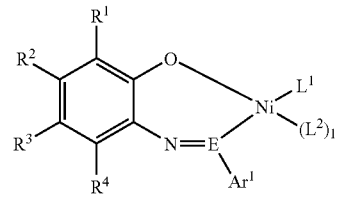

8

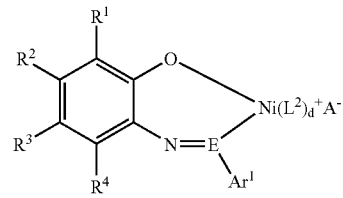

9

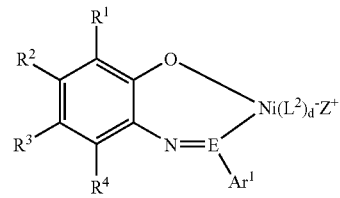

10

E is nitrogen or phosphorus;
Ar¹ is selected from the group consisting of:

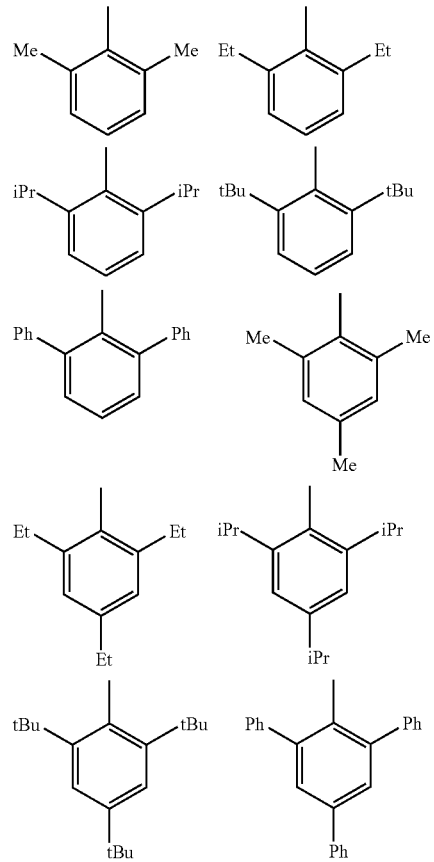

-continued

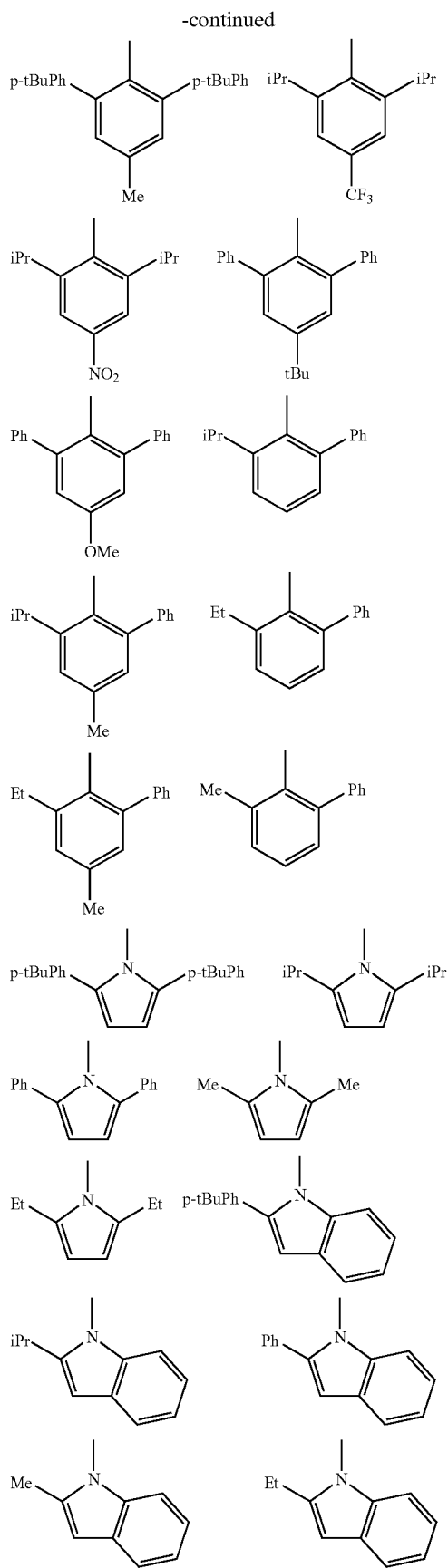

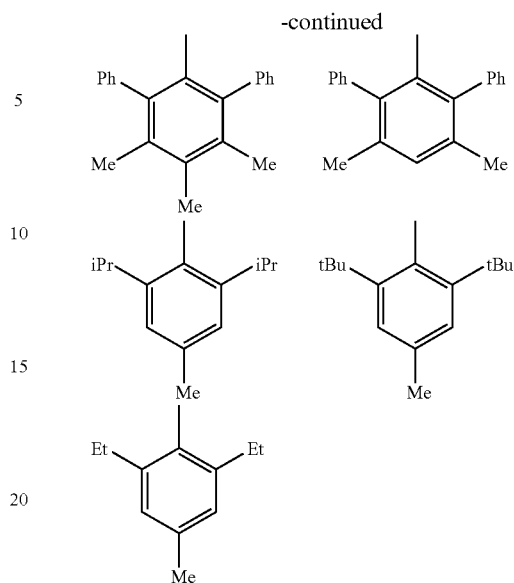

$R^1$–$R^4$ are each independently hydrogen, a hydrocarbyl, a substituted a hydrocarbyl or a functional group, provided that $R^3$ and $R^4$ do not form a naphthyl ring;

$L^1$ represents a formal anionic ligand selected from the group consisting of ZETA-FORMAL ANIONIC LIGANDS;

$L^2$ represents a formal neutral ligand selected from the group consisting of ZETA-FORMAL NEUTRAL LIGANDS;

"d" is 1, 2 or 3;

$A^-$ is an anion that may or may not coordinate to Ni; and $Z^+$ is a cation selected from the group consisting of metals or metal complexes of groups 1, 2, 11, and 12, Where Me is methyl, Et is ethyl, iPr is isopropyl, tBu is tertiary butyl, Ph is phenyl, p-t-BuPh is para-tertiary-butylphenyl.

19. The composition of claim 18 wherein $A^-$ is a non-coordinating anion.

20. The composition of claim 18 wherein $A^-$ is selected from the group consisting of halides, carboxylates, phosphates, sulfates, sulfonates, borates, aluminates, alkoxides, thioalkoxides, anonic substituted hydrocarbons, and anionic metal complexes.

21. A composition represented by formula:

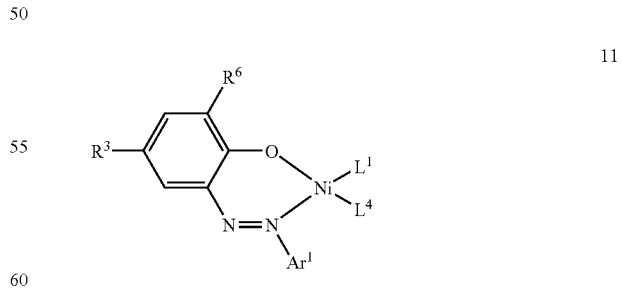

11 wherein
$L^1$ represents a formal anionic ligand;
$R^3$ is hydrogen, a hydrocarbyl, a substituted hydrocarbyl or a functional group;
$R^6$ is $C(R^7)_e$,
e is 2 or 3, R⁷ is a hydrocarbon, a substituted hydrocarbon, or a functional group, two R⁷ groups may be part of a common arene ring when e is 2;
Ar¹ is an arene; and
L⁴ is a formal neutral ligand, coordinated to the nickel in addition to the nitrogen of the azo-phenoxide ligand.

22. The composition of claim 21 wherein L⁴ selected from the group consisting of:

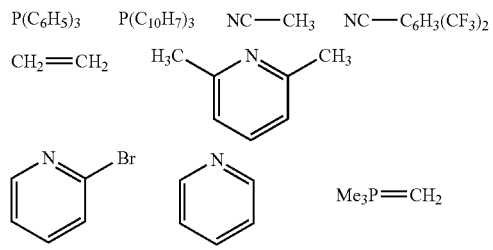

where Me is methyl.

23. The composition of claim 22 wherein R⁶ is selected from the group consisting of t-butyl, adamantyl, phenyl, naphthyl, and anthracenyl.

24. A composition represented by the formula:

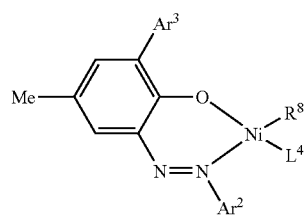

wherein:
L⁴ represents a formal neutral ligand based on carbon, nitrogen or phosphorus;
R⁸ represents a formal anionic ligand which may be hydrogen or a hydrocarbyl;
Ar² is a phenyl group independently substituted in the 2 and 6 positions by secondary hydrocarbons, secondary substituted hydrocarbons, tertiary hydrocarbons, tertiary substituted hydrocarbons, or arenes
Ar² is an arene;
Ar³ is an arene; and
Me is methyl.

25. The composition of claim 24 wherein Ar² is selected from the group

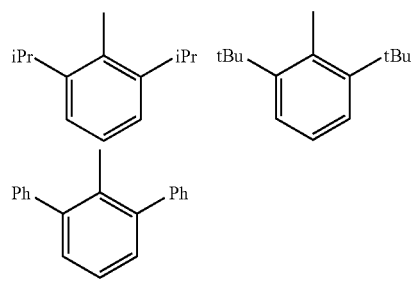

consisting of:
where iPr is isopropyl, tBu is tertiary butyl and Ph is phenyl.

26. The composition of claim 24 wherein Ar³ is selected from the group consisting of:

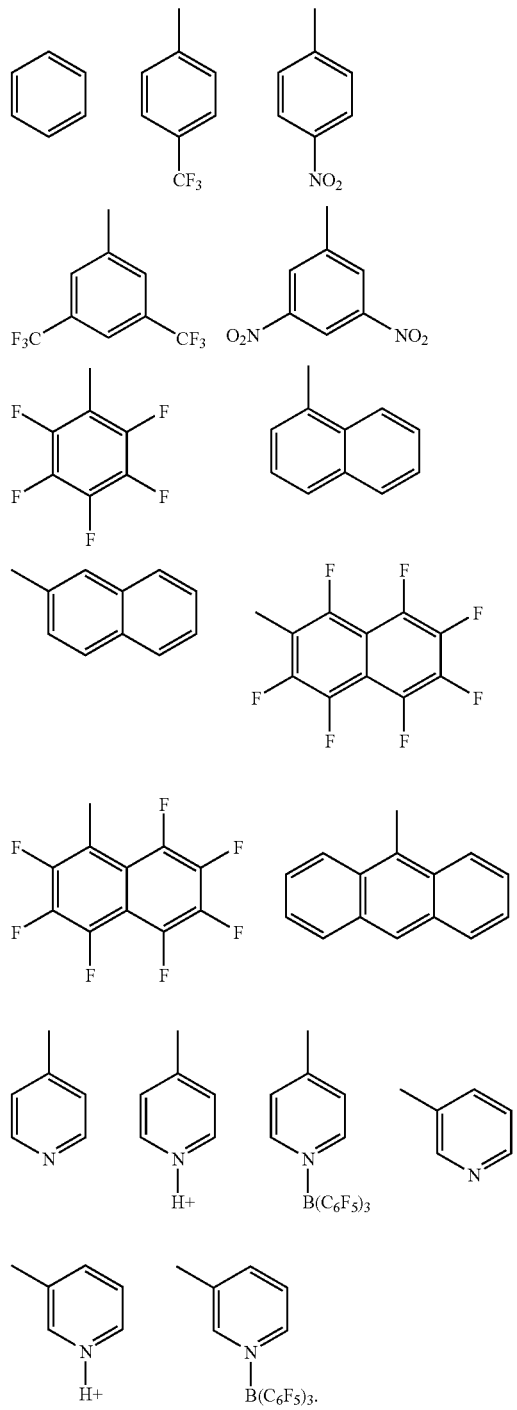

27. The composition of claim 24 wherein R⁸ is selected from the group consisting of hydrogen, a hydride, methyl, ethyl, trimethylsilylmethyl, trimethylsilyl, phenyl, naphthyl, allyl and benzyl.

28. A composition represented by the formula:

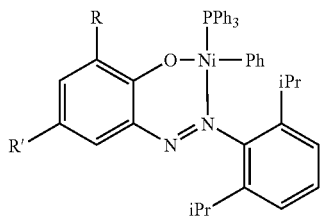

where R is tertiary butyl or anthracene and R' is methyl or tertiary butyl, iPr is isopropyl and Ph is phenyl.

29. A process to oligomerize unsaturated monomers comprising combining monomer, activator and the composition of claim 1.

30. A process to polymerize olefins comprising combining olefins, activator and the composition of claim 1.

31. A process to oligomerize unsaturated monomers comprising combining monomer and the composition of claim 1.

32. A process to polymerize olefins comprising combining olefins and the composition of claim 1.

* * * * *